(12) United States Patent
Rosenfeld et al.

(10) Patent No.: US 7,395,216 B2
(45) Date of Patent: *Jul. 1, 2008

(54) USING PREDICTIVE MODELS TO CONTINUOUSLY UPDATE A TREATMENT PLAN FOR A PATIENT IN A HEALTH CARE LOCATION

(75) Inventors: Brian A. Rosenfeld, Baltimore, MD (US); Michael Breslow, Lutherville, MD (US)

(73) Assignee: VISICU, Inc., Baltimore, MD (US)

( * ) Notice: Subject to any disclaimer, the term of this patent is extended or adjusted under 35 U.S.C. 154(b) by 71 days.

This patent is subject to a terminal disclaimer.

(21) Appl. No.: 11/444,080

(22) Filed: May 31, 2006

(65) Prior Publication Data
US 2006/0271407 A1  Nov. 30, 2006

Related U.S. Application Data

(63) Continuation-in-part of application No. 10/654,668, filed on Sep. 4, 2003, and a continuation-in-part of application No. 10/946,548, filed on Sep. 21, 2004, now Pat. No. 7,256,708.

(60) Provisional application No. 60/141,520, filed on Jun. 23, 1999.

(51) Int. Cl.
    *G06Q 10/00* (2006.01)
(52) U.S. Cl. .................. 705/2; 705/3; 600/300
(58) Field of Classification Search .......... 705/2–3; 600/300
    See application file for complete search history.

(56) References Cited

U.S. PATENT DOCUMENTS 3,646,606 A * 2/1972 Buxton et al. ............. 600/483
4,365,199 A   12/1982 McNair
4,489,387 A   12/1984 Lamb et al.
4,731,725 A    3/1988 Suto et al.

(Continued)

FOREIGN PATENT DOCUMENTS

WO    WO 98/29790    7/1998

(Continued)

OTHER PUBLICATIONS

Terry Ann Capuano et al. Remote Telemetry, Jul. 1995, Nursing Management, vol. 26, No. 7, p. 26.*

(Continued)

*Primary Examiner*—Robert W Morgan
(74) *Attorney, Agent, or Firm*—Roberts Mardula & Wertheim, LLC

(57) ABSTRACT

A system for determining a treatment plan for a patient comprises a database of patient data elements indicative of a medical condition associated with a patient. A predictive model is applied to patient assessment data and used to prepare a treatment plan. A rules engine applies a patient rule consistent with the treatment plan to selected data elements stored in the database to produce an output indicative of a change in the medical condition of the patient. The output from the rules engine is used to determine if intervention is warranted. The predictive model is applied continuously to determine whether to update the treatment plan and, if necessary, the patient rule.

58 Claims, 9 Drawing Sheets

U.S. PATENT DOCUMENTS

| | | | |
|---|---|---|---|
| 4,838,275 A | 6/1989 | Lee | |
| 4,852,570 A | 8/1989 | Levine | |
| 4,878,175 A | 10/1989 | Norden-Paul et al. | |
| 5,255,187 A | 10/1993 | Sorensen | |
| 5,321,800 A | 6/1994 | Lesser | |
| 5,348,008 A | 9/1994 | Bornn et al. | |
| 5,544,649 A | 8/1996 | David et al. | |
| 5,544,661 A | 8/1996 | Davis et al. | |
| 5,574,828 A | 11/1996 | Hayward et al. | |
| 5,576,952 A | 11/1996 | Stutman et al. | |
| 5,619,991 A | 4/1997 | Sloane | |
| 5,678,562 A | 10/1997 | Sellers | |
| 5,701,894 A | 12/1997 | Cherry et al. | |
| 5,715,449 A | 2/1998 | Peters, Jr. et al. | |
| 5,724,580 A | 3/1998 | Levin et al. | |
| 5,729,204 A | 3/1998 | Fackler et al. | |
| 5,772,585 A | 6/1998 | Lavin et al. | |
| 5,812,983 A | 9/1998 | Kumagai | |
| 5,822,544 A | 10/1998 | Chaco et al. | |
| 5,823,948 A | 10/1998 | Ross, Jr. et al. | |
| 5,832,450 A | 11/1998 | Myers et al. | |
| 5,839,438 A | 11/1998 | Graettinger et al. | |
| 5,842,978 A | 12/1998 | Levy | |
| 5,867,821 A | 2/1999 | Ballantyne et al. | |
| 5,868,669 A | 2/1999 | Iliff | |
| 5,899,855 A | 5/1999 | Brown | |
| 5,942,986 A | 8/1999 | Shabot et al. | |
| 5,987,519 A | 11/1999 | Peifer et al. | |
| 6,024,699 A | 2/2000 | Surwit et al. | |
| 6,093,146 A | 7/2000 | Filangeri | |
| 6,102,856 A | 8/2000 | Groff et al. | |
| 6,154,668 A | 11/2000 | Pedersen et al. | |
| 6,168,563 B1 | 1/2001 | Brown | |
| 6,215,403 B1 | 4/2001 | Chan et al. | |
| 6,225,901 B1 | 5/2001 | Kail, IV | |
| 6,230,142 B1 | 5/2001 | Begnino et al. | |
| 6,234,964 B1 | 5/2001 | Iliff | |
| 6,238,338 B1 | 5/2001 | DeLuca et al. | |
| 6,245,013 B1 | 6/2001 | Minoz et al. | |
| 6,254,536 B1 | 7/2001 | Devito | |
| 6,278,999 B1 | 8/2001 | Knapp | |
| 6,292,698 B1 | 9/2001 | Duffin et al. | |
| 6,304,788 B1 | 10/2001 | Eady et al. | |
| 6,315,719 B1 | 11/2001 | Rode et al. | |
| 6,364,834 B1 | 4/2002 | Reuss et al. | |
| 6,385,589 B1 | 5/2002 | Trusheim et al. | |
| 6,398,728 B1 | 6/2002 | Bardy | |
| 6,442,433 B1 | 8/2002 | Linberg | |
| 6,533,724 B2 | 3/2003 | McNair | |
| 6,741,264 B1 | 5/2004 | Lesser | |
| 6,835,176 B2 | 12/2004 | McNair | |
| 6,893,396 B2 | 5/2005 | Schulze et al. | |
| 2002/0002473 A1 | 1/2002 | Schrier et al. | |
| 2002/0177758 A1 | 11/2002 | Schoenberg et al. | |
| 2002/0177759 A1 | 11/2002 | Schoenberg et al. | |
| 2002/0187483 A1 | 12/2002 | Hoffman et al. | |
| 2002/0193667 A1 | 12/2002 | McNair | |
| 2003/0036687 A1 | 2/2003 | Schoenberg et al. | |
| 2004/0030578 A1 | 2/2004 | Cross et al. | |
| 2004/0063031 A1 | 4/2004 | Gallucci et al. | |
| 2004/0078366 A1 | 4/2004 | Crooks et al. | |
| 2004/0193451 A1 | 9/2004 | McNair | |
| 2004/0197813 A1 | 10/2004 | Hoffman et al. | |
| 2004/0199333 A1 | 10/2004 | Hoffman et al. | |
| 2004/0225201 A1 | 11/2004 | McNair | |
| 2004/0236604 A1 | 11/2004 | McNair | |
| 2005/0027563 A1 | 2/2005 | Fackler et al. | |
| 2005/0049891 A1 | 3/2005 | Wilson | |
| 2005/0060191 A1 | 3/2005 | Parkins et al. | |
| 2005/0075794 A1 | 4/2005 | Hoffman et al. | |
| 2005/0075904 A1 | 4/2005 | Wagner et al. | |
| 2005/0076060 A1 | 4/2005 | Finn et al. | |
| 2005/0125098 A1 | 6/2005 | Wang et al. | |
| 2005/0125256 A1 | 6/2005 | Schoenberg et al. | |
| 2005/0206518 A1 | 9/2005 | Welch et al. | |
| 2005/0228241 A1 | 10/2005 | McNair | |
| 2005/0251418 A1 | 11/2005 | Fox, Jr. et al. | |
| 2005/0267351 A1 | 12/2005 | Humphrey et al. | |
| 2005/0283062 A1 | 12/2005 | Hoffman et al. | |
| 2006/0031018 A1 | 2/2006 | Bush et al. | |
| 2006/0036542 A1 | 2/2006 | McNair | |

FOREIGN PATENT DOCUMENTS

| | | |
|---|---|---|
| WO | WO 99/13766 | 3/1999 |
| WO | 00/79466 A2 | 12/2000 |

OTHER PUBLICATIONS

Editors: M. Michael Shabot and Reed M. Gardner, Computers and Medicine: Decision Support Systems in Critical Care, 1994, Springer-Verlag New York, Inc. New York.

Gilad J. Kuperman, M.D. and Reed M. Gardner, Ph.D., The Help System: A Snapshot in Time, 1988, Dept. of Biophysics, LDS Hospital, Salt Lake City, Utah.

Project Leaders: Benoit Dawant, Ph.D. and John A. Morris, Jr. M.D., Vanderbilt University Simon Project Website, 2004, Vanderbilt University, Nashville, Tennessee.

Greg Borzo, Web Technology: Coming Soon to a Hospital Near You, American Medical News, Nov. 18, 1996, American Medical Association www.amednews.com.

ABSTRACT: J.E. Gray, C. Safran, R.B. Davis, G. Pomilio-Weitzner, J.E. Stewart, L. Zaccagnini and D. Pursley, Baby Care Link: Using the Internet and Telemedicine to Improve Care for High-risk Infants, Dec. 2000, Pediatrics, vol. 106, No. 6, pp. 1318-1324.

ABSTRACT: Ray Duncan and Jeffrey J. Pomerance, Computer Assistance in Delivery of Patient Care in a Neonatal Intensive Care Unit, The Use of Computers in Perinatal Medicine, Chapter 19, pp. 337-351, 1982, Praeger Publishers, New York, NY.

ABSTRACT: Ray Duncan, MD, Computer Assisted Care in the Neonatal Intensive Care Unit, Proceedings of the 17th Annual Symposium on Computer Applications in Medical Care, Nov. 1993, p. 929, American Medical Informatics Association.

ABSTRACT: Metnitz PG, Laback P. Popow C, Laback 0, Lenz K, Hiesmayr M, Computer assisted data analysis in intensive care: the ICDEV project—development of a scientific database system for intensive care (Intensive Care Data Evaluation Project), International Journal of Clinical Monitoring and Computing, 1995, vol. 12, No. 3, pp. 147-159.

ABSTRACT: Paul H. Peristein, MD, Neil K. Edwards, MS, Harry D. Atherton, MS, James M. Sutherland, MD, Computer Assisted Newborn Intensive Care, Pediatrics, Apr. 1976, vol. 57, No. 4, pp. 494-501.

ABSTRACT: Edward H. Shortliffe, MD, PHD, Computer Programs to Support Clinical Decision Making, JAMA, Jul. 3, 1987, vol. 258, No. 1, pp. 61-66.

ABSTRACT: Merz U, Peschgens T, Budde R, Kretzschmann F, Homchen H V, Computer-assisted monitoring in the neonatal intensive care unit [German], Klin Padiatr, Nov./Dec. 1995, vol. 207, No. 6, pp. 331-333.

ABSTRACT: Charles Safran, MD, Francois Herrman, MD, David Rind, MD, Hollis B. Kowaloff, BA, Howard L. Bleich, MD, and Warner V. Slack, MD, Computer-Based Support for Clinical Decision Making, M.D. Computing, 1990, vol. 7, No. 5, pp. 319-322.

ABSTRACT: Reed M. Gardner, PHD, Computerized Management of Intensive Care Patients, M.D. Computing, 1986, vol. 3, No. 1, pp. 36-51.

ABSTRACT: F. John Lewis; Steven Deller; Michael Quinn; Benjamin Lee; Raymond Will; and John Raines, Continuous Patient Monitoring with a Small Digital Computer, Computers and Biomedical Research, 1972, vol. 5, pp. 411-428.

ABSTRACT: N. Fumai, C. Collet, M. Petroni, K. Roger, A. Lam, E. Saab, A. 'S. Malowany, F. A. Carnevale, R. D. Gottesman, Database Design of an Intensive Care Unit Patient Data Management System, Proceedings of the Fourth Annual IEEE Symposium on Computer-Based Medical Systems, May 12, 1991, pp. 78-85, IEEE Computer Society Press, Los Alamitos, CA.

ABSTRACT: George Hripcsak; Paul D. Clayton; Robert A. Jenders; James J. Cimino; and Stephen B. Johnson, Design of a Clinical Event Monitor, Computers and Biomedical Research, Jun. 1996, vol. 29, No. 3, pp. 194-221.

ABSTRACT: David M. Rind, MD; Roger Davis, SCD; and Charles Safran, MD, Designing Studies of Computer-Based Alerts and Reminders, MD Computing, 1995, vol. 12, No. 2, pp. 122-126.

ABSTRACT: Dwayne R. Westenkow, PHD, Automating Patient Care with Closed-Loop Control, M.D. Computing, 1986, vol. 3, No. 2, pp. 14-20.

ABSTRACT: Snowden S, Brownlee KG, Dear P R, An expert system to assist neonatal intensive care, I Med Eng Technol Mar.-Apr. 1997;21(2):67-73, vol. 21, No. 2, pp. 67-73.

ABSTRACT: A. Aifredo Morales, Engr., MS , James Gray, MD, MS , Charles Safran, MD, An Application Server Approach for Integration of Clinical Systems, Proceedings of the AMIA 1999 Annual Symposium, 1999, AMIA.

ABSTRACT: Kang Wang, PHD; Isaac Kohane, MD, PHD; Karen L. Bradshaw , BS; James Facider, MD, A Real Time Patient Monitoring System on the World Wide Web, Proceedings of the 1996 AMIA Annual Fall Symposium, Nov. 1996, pp. 729-732, Hanley and Belfus, Inc.

ABSTRACT: Michael Factor, David H. Gelernter, Craig E. Kolb, Perry L. Miller and Dean F. Sittig, Real-Time Data Fusion in the Intensive Care Unit, IEEE Computer, Nov. 1991, pp. 45-53.

Editor: Judy G. Ozbolt, Ph.D., A Conference of the American Medical Informatics Association, Symposium on Computer Applications in Medical Care, Nov. 5-9, 1994, Hanley & Belfus, Inc. Medical Publishers, Philadelphia, PA.

W. Hsueh-Fen Young, Reed M. Gardner, Thomas D. East and Kristi Turner, Computerized Ventilator Data Selection: Artifact Rejection and Data Reduction, Int'l Journal of Clinical Monitoring and Computing 1997, 14: 165-176, Kluwer Academic Publishers, Netherlands.

Randolph A. Miller, M.D. and Reed M. Gardner, Ph.D., Summary Recommendations for Responsible Monitoring and Regulation of Clinical Software Systems, Annals of Internal Medicine, Nov. 1997, vol. 127, No. 9.

Reed M. Gardner, T. Allan Pryor and Homer R. Warner, The HELP Hospital Information System: Update 1998, Intl Journal of Medical Informatics 1999, vol. 54, pp. 169-182, Elsevier Science Ireland Ltd., Ireland.

Martin Spikoff, Systems Aid Rural Health Delivery, QIPhysician.com, Sep. 2003.

ABSTRACT: Jerome P. Kassirer, MD, The Next Transformation in the Delivery of Health Care (Editorial), NEJM, Jan. 5, 1995, vol. 332, No. 1, pp. 52-54.

ABSTRACT: Lorene S. Avila; M. Michael Shabot, Keys to the successful implementation of an ICU patient data management system, International Journal of Clinical Monitoring and Computing, 1988, vol. 5, pp. 15-25.

ABSTRACT: Reed M. Gardner, MD; M. Michael Shabot, MD, Computerized ICU Data Management: Pitfalls and Promises, International Journal of Clinical Monitoring and Computing, 1990, vol. 7, pp. 99-105.

Karl W. Thomas, M.D., Charles S. Dayton, B.S., R.Ph., and Michael W. Peterson, M.D., Evolution of Internet-Based Clinical Decision Support Systems, Journal of Medical Internet Research 1999, vol. 1, University of Iowa, Iowa City, Iowa.

ABSTRACT: C. J. McDonald, Protocol-Based Computer Reminders, The Quality of Care and The Non-Perfectability of Man, The New England Journal of Medicine, Dec. 9, 1976, vol. 295, No. 24, 1351-1355.

ABSTRACT: T.D. East, A.H. Morris, C.J. Wallace, T.P. Clemmer, J.F. Orme, Jr., L.K. Weaver, S. Henderson and D.F. Sittig, A Strategy for Development of Computerized Critical Care Decision Support Systems, Intl Journal of Clinical Monitoring and Computing, 1991-92, vol. 8, No. 4, 263-269.

Dr. Ramana Reddy and Dr. V. "Juggy" Jagannathan, Secure Collaboration Technology for Rural Clinical Telemedicine, National Library of Medicine, Oct. 8, 1996 Press Release, West Virginia University, West Virginia.

West Virginia University Research Corporation, Secure Collaboration Technology for Rural Clinical Telemedicine: Final Report, National Library of Medicine.

Martin J. Tobin, M.D., Principles and Practice of Intensive Care Monitoring, 1998, McGraw-Hill Inc.

Peter J. Haug, Reed M. Gardner, and R. Scott Evans, "Hospital-Based Decision Support" in *Clinical Decision Support Systems: Theory and Practice*, Eta S. Berner [ed.], 1999, Springer-Verlag New York, Inc., New York, NY, pp. 77-103.

Clement J. McDonald, M.D. and William M. Tierney, M.D., Computer-Stored Medical Records: Their Future Role in Medical Practice, JAMA, Jun. 17, 1988, pp. 3433-3440, vol. 259, No. 23.

Gilad J. Kuperman, Reed M. Gardner, and T. Allan Pryor, HELP: A Dynamic Hospital Information System, 1991, Springer-Verlag New York, Inc., New York, NY.

M. Michael Shabot, M.D., Mark Lobue, B.S., and Jeannie Chen, Pharm.D., Wireless Clinical Alerts for Physiologic, Laboratory and Medication Data, Department of Enterprise Information Services, Surgery and Pharmacy Cedars-Sinai Health System, Los Angeles, CA.

Chaoxin Sima, Ravi Raman, Ramana Reddy, William Hunt and Sumitra Reddy, Vital Signs Services for Secure Telemedicine Applications, Concurrent Engineering Research Center, West Virginia University, Morgantown, WV.

Dickey Seidlitz Johnson, Jane Ranzenberger, Ruth D. Herbert, Reed M. Gardner, and Terry P. Clemmer, A Computerized Alert Program for Acutely Ill Patients, Journal of Nursing Administration, Jun. 1980, pp. 26-35.

Reed M. Gardner, Ph.D., Blair J. West, M.S., T. Allan Pryor, Ph.D., Keith G Larsen, R.Ph., Homer R Warner, M.D., Terry P Clemmer, M.D., James F. Orme, Jr. M.D., Computer-Based ICU Data Acquisition as an Aid to Clinical Decision-Making, Critical Care Medicine, 1982, pp. 823-830, vol. 10, No. 12, The Williams & Wilkins Co.

Reed M. Gardner and Terry P. Clemmer, Computerized Protocols Applied to Acute Patient Care, 1977, Mediad Inc., Tarrytown, NY.

Karen E. Bradshaw , Reed M. Gardner, and T. Allan Pryor, Development of a Computerized Laboratory Alerting System, Computers and Biomedical Research 22, 575-587, 1989, Academic Press, Inc.

Terry P. Clemmer and Reed M. Gardner, Medical Informatics in the Intensive Care Unit: State of the Art 1991, International Journal of Clinical Monitoring and Computing 8: 237-250, 1992, Kluwer Academic Publishers, Netherlands.

Reed M. Gardner, Ph.D., David V. Ostler, and O. Hank Duffy , M.D., Computers in the Emergency Room, Internal Medicine for the Specialist, vol. 8, No. 3, Mar. 1987.

Dean F. Sittig, Nathan L. Pace, Reed M. Gardner, Eduardo Beck, and Alan H. Morris, Implementation of a Computerized Patient Advice System Using the HELP Clinical Information System, Computers and Biomedical Research 22, 474-487, 1989, Academic Press Inc.

P. D. Clayton, R. Scott Evans, T. Pryor, R. M. Gardner, P. J. Haug, O. B. Wigertz, and H. R. Warner, Bringing HELP to the Clinical Laboratory—Use of an Expert System to Provide Automatic Interpretation of Laboratory Data, Ann Clin Biochem 1987; 24: Supplement.

D. F. Sittig, Ph.D., R. M. Gardner, Ph.D., N. L. Pace, M.D., M. Bombino, M. D., and A. H. Morris, M.D., Compas: A Computerized Patient Advice System to Direct Ventilatory Care, Medical Informatics 88: Computers in Clinical Medicine, Sep. 13-15, 1988, British Medical Informatics Society, London.

Karen E. Bradshaw, Ph.D., Dean F. Sittig, Ph.D., Reed M. Gardner, Ph.D., T. Alllan Pryor, Ph.D., and Marge Budd, M.S., Improving Efficiency and Quality in a Computerized ICU, 1988 SCAMC, Inc.

Dean F. Sittig, Ph.D., C. Gregory Elliott, M.D., C. Jane Wallace, R.N., B.S.N., Polly Bailey, R.N., Reed M. Gardner, Ph.D., Computerized Screening for Identification of Adult Respiration Distress Syndrome (ARDS) Patients, 1988 SCAMC, Inc.

R. Scott Evans, Ph.D., Reed M. Gardner, Ph.D., John P. Burke, M.D., Stanley L. Pestotnik, R.P.H., Robert A. Larsen, M.D., David C.

Classen, M.D., and Paul D. Clayton, Ph.D., A Computerized Approach to Monitor Prophylactic Antibiotics, 1987, SCAMC, Inc.

Susan Henderson, B.A., Thomas D. East, Ph.D., Alan H. Morris, M.D., Reed M. Gardner, Ph.D., Performance evaluation of computerized clinical protocols for management of arterial hypoxemia in ARDS patients, LDS Hospital, and University of Utah, Salt Lake City, UT.

Thomas D. East, Ph.D., Susan Henderson, B.A., Alan H. Morris, M.D., Reed M. Gardner, Ph.D., Implementation Issues and Challenges for Computerized Clinical Protocols for Management of Mechanical Ventilation in ARDS Patients, LDS Hospital, Salt Lake City, UT.

C. Gregory Elliott, M.D., Deon Simmons, R.R.T., C. Duwayne Schmidt, M.D., Kip Enger, B.S., C.R.T.T., Loren Greenway, B.S., R.R.T., and Reed M. Gardner, Ph.D., Computer-Assisted Medical Direction of Respiratory Care, Respiratory Management, vol. 19, No. 2.

H. Keller and Ch. Trendelenburg, Data Presentation Interpretation, Clinical Biiochemistry Principles, Methods, Applications, WalterdeGruyter & Co., 1989.

Reed M. Gardner, Ph.D., Karen W. Hollingsworth, R.N., M.S, C.C.R.N., ECG and Pressure Monitoring: How to Obtain Optimal Results, 295-305.

Reed M. Gardner, Ph.D., Dean F. Sittig, M.S., Marge C. Budd, R.N., M.S., Computers in the Intensive Care Unit: Match or Mismatch?, 248-259.

Emmanuel Furst, Ph.D., Cardiovascular Technology, The Journal of Cardiovascular Nursing, Nov. 1989, 68-78.

Dean F. Sittig, Reed M. Gardner, Nathan L. Pace, Alan H. Morris, and Eduardo Beck, Computerized Management of Patient Care in a Complex, Controlled Clinical Trial in the Intensive Care Unit, Computer Methods and Programs in Biomedicine 30, 1989, 77-84.

Karen E. Bradshaw, Ph.D., Dean F. Sittig, Ph.D., Reed M. Gardner, Ph.D., T. Allan Pryor, Ph.D., and Marge Budd, R.N., M.S., Computer-Based Data Entry for Nurses in the ICU, Clinical Computing, Nov. 1988.

Robert A. Larsen, M.D., R. Scott Evans, Ph.D., John P. Burke, M.D., Stanley L. Pestonik, R.Ph., Reed M. Gardner, Ph.D., David C. Classen, M.D., Improved Perioperative Antibiotic Use and Reduced Surgical Wound Infections Through Use of Computer Decision Analysis, Computer Applications for Surgical Prophylaxis/Larsen et al.

R. M. Gardner, Computers in the ICU and Surgery-Keeping Real-Time Patient Records for Decision-Making.

Thomas D. East, Ph.D., Alan H. Morris, M.D., Terry Clemmer, M.D., James F. Orme, M.D., C. Jane Wallace, B.S.N., Susan Henderson, B.A., Dean F. Sittig, Ph.D., Reed M. Gardner, Ph.D., Development of Computerized Critical Care Protocols—A Strategy That Really Works!, 1990 LDS Hospital, Salt Lake City, UT.

R. Scott Evans, Ph.D., John P. Burke, M.D., Stanley L. Pestonik, R.Ph., David C. Classen, M.D., Ronald L. Menlove, Ph.D., and Reed M. Gardner, Ph.D., Prediction of Hospital Inflections and Selection of Antibiotics Using an Automated Hospital Database, 1990, SCAMC, Inc. 663-667.

Susan E. Henderson, B.A., Robert O. Crapo, M.D., Thomas D. East, Ph.D., Alan H. Morris, M.D., C. Jane Wallace, R.N., Reed M. Gardner, Ph.D., Computerized Clinical Protocols in an Intensive Care Unit: How Well are They Followed?, 1990, SCAMC, Inc., LDS Hospital, Salt Lake City, UT.

Reed M. Gardner, PHD, Russell K. Hulse, RPH, MBA, Keith G. Larsen, RPH, Assessing The Effectiveness Of A Computerized Pharmacy System, 1990, SCAMC, Inc., 668-672.

Reed M. Gardner, "Patient-Monitoring Systems", *Medical Informatics: Computer Applications in Health Care*, E.H. Shortliffe and L.E. Perrealt (eds.), G. Wiederhold and L.M. Fagan (assoc. eds.) (Reading, MA: Addison-Wesley, 1990.

Reed M. Gardner, Olaf K. Golubjatnikov, R. Myron Laub, Julie T. Jacobson, and R. Scott Evans, Computer-Critiqued Blood Ordering Using the HELP System, Computers and Biomedical Research 23, 514-528, 1990, Academic Press, Inc.

Karen E. Tate, Ph.D., Reed M. Gard'ner, Ph.D., and Lindell K. Weaver, M.D., A Computerized Laboratory Alerting System, Clinical Computing, 1990, vol. 7, No. 5, 296-301.

Dean F. Sittig, Reed M. Gardner, Alan H. Morris, and C. Jane Wallace, Clinical Evaluation of Computer-Based Respiratory Care Algorithms, International Journal of Clinical Monitoring and Computing 7, 1990, 177-185, Kluwer Academic Publishers, Netherlands.

R. Scott Evans, Stanley L. Pestotnilc, John P. Burke, Reed M. Gardner, Robert A. Larsen, and David C. Classen, Reducing Tile Duration Of Prophylactic Antibiotic Use Through Computer Monitoring Of Surgical Patients, DICP, The Annals of Pharmacotherapy, Apr. 1990, vol. 24, 351-354, Harvey Whitney Books Company, Cincinnati, OH.

Reed M. Gardner, and M. Michael Shabot, Computerized ICU Data Management: Pitfalls and Promises, International Journal of Clinical Monitoring and Computing 7: 99-105, 1990, Kluwer Academic Publishers, Netherlands.

Stanley L. Pestotnik, R.Ph., R. Scott Evans, Ph.D., John P. Burke, M.D., Reed M. Gardner, Ph.D., David C. Classen, M.D., Therapeutic Antibiotic Monitoring: Surveillance Using a Computerized Expert System, The American Journal of Medicine, Jan. 1990, vol. 88, 43-48.

Gil Kuperman, MD, Brent James, MD, MSTAT, Julie Jacobsen, MT (ASCP), Reed M. Gardner, PHD, Continuous Quality Improvement Applied To Medical Care: Experiences At LDS Hospital, Medical Decision Making, Oct-Dec. 1991, 60-65, vol. 11, No. 4.

Susan Henderson, Robert O. Crapo, C. Jane Wallace, Thomas D. East, Alan H. Morris & Reed M. Gardner, Performance Of Computerized Protocols For The Management Of Arterial Oxygenation In An Intensive Care Unit, International Journal of Clinical Monitoring and Computing 8, 1992, 271-180, Kluwer Academic Publishers, Netherlands.

Reed M. Gardner, Ph.D., William L. Hawley, Thomas D. East, Ph.D., Thomas A. Oniki, B.S., Hsueh-Fen W. Young, B.S., Real Time Data Acquisition: Experience With the Medical Information Bus (MIB), LDS Hospital, University of Utah, Salt Lake City, UT.

Eric F. Lepage, MD, Reed M. Gardner, PHD, R. Myron Laub, MD, Julie T. Jacobson, MT(ASCP), Assessing The Effectiveness Of A Computerized Blood Order Consultation System, LDS Hospital, 1992, 33-37, AMIA, Inc.

R. Scott Evans, Ph.D., Stanley L. Pestotnik, R.Ph., David C. Classen, M.D., Sheron B. Bass, B.S.N. Ronald L. Menlove, Ph.D., Reed M. Gardner, Ph.D., and John P. Burke, M.D., Development Of A Computerized Adverse Drug Event Monitor, LDS Hospital and University of Utah, Salt Lake City, UT.

E. Lepage, R. Traineau, Ph. Marchetti, M. Benbunan, R. M. Gardner, Development Of A Computerized Knowledge Based System Integrated To A Medical Workstation: Application To Blood Transfusion, MEDINFO, 1992, 585-590, Elsevier Science Publishers B.V.

Reed M. Gardner, Ph.D. and R. Scott Evans, Ph.D., Computer-Assisted Quality Assurance, Group Practice Journal, May/Jun. 1992, 41(3), 8-11.

Thomas D. East, Ph.D., W. Hsueh-Fen Young, M.S., and Reed M. Gardner, Ph.D., Digital Electronic Communication between ICU Ventilators and Computers and Printers, Respiratory Care, Sep. 1992, vol. 37 No. 9, 1113-1123.

Reed M. Gardner, Computers in Critical Care, Wellcome Trends in Hospital Pharmacy, Jul. 1992.

T. Allan Pryor, Reed M. Gardner and W. Clinton Day, Computer System for Research and Clinical Application to Medicine, AFIPS—Conference Proceedings, vol. 33, 1968, 809-816.

Homer R. Warner, M.D., Reed M. Gardner and Alan F. Toronto, M.D., Computer-Based Monitoring of Cardiovascular Functions in Postoperative Patients, Supplement II to Circulation, Apr. 1968, vols. 37 & 38, 68-74.

Russell M. Nelson, Homer R. Warner, Reed E. Gardner and J. D. Mortensen, Computer Based Monitoring of Patients Following Cardiac Surgery, Computers in Cardiology, Jul.-Aug. 1969, vol. 5, No. 4, 926-930.

Reed M. Gardner, Computerized Patient Monitoring at LDS Hospital—An Evaluation, Proceedings of the San Diego Biomedical Symposium, 1971, vol. 10, 151-159.

Reed M. Gardner, Monitoring of Physiological Data in a Clinical Environment, Annual Review of Biophysics and Bioengineering, 1972, vol. 1, 211-224.

Reed M. Gardner, Computerized Intensive Care Monitoring at LDS Hospital—Progress and Development, 97-105.

Reed M. Gardner, Donald R. Bennet, and Richard B Vorce, Eight-Channel Data Set for Clinical EEG Transmission Over Dial-Up Telephone Network, IEEE Transactions on Biomedical Engineering, May 1974, vol. BME-21, No. 3, 246-249.

Reed M. Gardner, George H. Cannon, Alan H. Morris, Kenneth R. Olsen, W. Gary Price, Computerized Blood Gas Interpretation and Reporting System, Computer Magazine, Jan. 1975, 39-45.

Russell K. Hulse, Stephen J. Clark, J. Craig Jackson, Homer R. Warner and Reed M. Gardner, Computerized Medication Monitoring System, American Journal of Hospital Pharmacy 33, Oct. 1976, 1061-1064.

Reed M. Gardner, Ph.D., Computers in the ICU, Medical Electronics, Jun. 1984, 129-135.

Robert D. Andrews, M.S., M.T., Reed M. Gardner, Ph.D., Sandy M. Metcalf, R.R.T., and Deon Simmons, R.R.T., Computer Charting: An Evaluation of a Respiratory Care Computer System, Respiratory Care, Aug. 1985, vol. 30, No. 8, 695-707.

Reed M. Gardner, Ph.D., Computerized Data Management and Decision Making in Critical Care, Symposium on Critical Care, Aug. 1985, vol. 65, No. 4, 1041-1051.

Reed M. Gardner, David P. Scoville, Blair J. West, Beth Bateman, Robert M. Cundick, Jr., Terry P. Clemmer, Integrated Computer Systems for Monitoring of the Critically Ill, 1977, 301-307.

T. Allan Pryor, Reed M. Gardner, Paul D. Clayton, Homer R. Warner, A Distributed Processing System for Patient Management, Computers in Cardiology, Sep. 1978, 325-328.

Reed M. Gardner, Ph.D., Terry P. Clemmer, M.D., Keith G. Larsen, R.Ph., and Dickey S. Johnson, R.N., Computerized Alert System Use in Clinical Medicine, IEEE Session 6, 1979, 136-140.

T. Allan Pryor, Homer R. Warner, Reed M. Gardner, HELP—A Total Hospital Information System.

T. P. Clemmer, R. M. Gardner, J. F. Orme, Jr., Computer Support in Critical Care Medicine, 1980.

Scott R. Cannon, and Reed M. Gardner, Experience with a Computerized Interactive Protocol System Using HELP, Computers and Biomedical Research 13, 1980, 399-409, Academic Press, Inc.

T. Allan Pryor, Paul D. Clayton, Reed M. Gardner, Randy Waki, and Homer R. Warner, HELP—A Hospital-Wide System for Computer-Based Support of Decision-Making, Jan. 1981.

T. A. Pryor, R. M. Gardner, P. D. Clayton and H. R. Warner, The HELP System, Proceedings of the Sixth Annual Symposium on Computer Applications in Medical Care, Oct.-Nov. 1982, 19-27, IEEE.

Reed M. Gardner, Information Management—Hemodynamic Monitoring, Seminars in Anesthesia, Dec. 1983, vol. 2, No. 4, 287-299.

T. A. Pryor, R. M. Gardner, P. D. Clayton, H. R. Warner, The HELP System, Journal of Medical Systems, 1983, vol. 7, No. 2, 87-102.

Reed M. Gardner, Blair J. West, T. Allan Pryor, Distributed Data Base and Network for ICU Monitoring, IEEE Computers in Cardiology, Sep. 18-24, 1984, 305-307.

Reed M. Gardner, T. Allan Pryor, Paul D. Clayton, and R. Scott Evans, Integrated Computer Network for Acute Patient Care, Symposium on Computer Applications in Medical Care, Nov. 4-7, 1984.

Reed M. Gardner, Tomorrow's Electronic Hospital is Here Today, IEEE Spectrum, Jun. 1984, 101-103.

Karen E. Bradshaw, Reed M. Gardner, Terry P. Clemmer, Jams F. Orme, Frank Thomas, and Blair J. West, Physicican Decision Making—Evaluation of Data Used in a Computerized ICU, International Journal of Clinical Monitoring and Computing I, 1984, 81-91.

Terry P. Clemmer, M.D., and Reed M. Gardner, Ph.D., Data Gathering, Analysis, and Display in Critical Care Medicine, Respiratory Care, Jul. 1985, vol. 30, No. 7, 586-601.

Reed M. Gardner, Ph.D., and William L. Hawley, Standardizing Communications and Networks in the ICU, Patient Monitoring and Data Management, 1985, 59-63.

R. Scott Evans, Reed M. Gardner, Allan R. Bush, John P. Burke, Jay A. Jacobson, Robert A. Larsen, Fred A. Meier, and Homer R. Warner, Development of a Computerized Infectious Disease Monitor (CIDM), Computers and Biomedical Research 18, 1985, 103-113.

Reed M. Gardner, Ph.D., Susan M. Monis, Paul Oehler, Monitoring Direct Blood Pressure: Algorithm Enhancements, 607-610.

R. Scott Evans, PhD, Robert A. Larsen, MD, John P. Burke, MD, Reed M. Gardner, PhD, Frederick A. Meier, MD, Jay A. Jacobson, MD, Marlyn T. Conti, BSN, Julie T. Jacobson, MT, Russell K. Hulse, RPH, Computer Surveillance of Hospital-Acquired Infections and Antibiotic Use, Journal of the American Medical Association, Aug. 22-29, 1986, vol. 256, No. 8, 1007-1011.

Reed M. Gardner, Computerized Management of Intensive Care Patients, Images, Signals, and Devices, 1986, vol. 3, No. 1.

R. Whiting, L. Hayes, The Practice of Telemedicine—The TARDIS Perspective, Informatics in Heatlhcare—Australia, Jul./Aug. 1997, vol. 6, No. 3, 103-106.

Monique Frize, Robin Walker, Clinical Decision-Support Systems for Intensive Care Units Using Case-Based Reasoning.

Ho Sung Lee, Seung Hun Park, and Eung Je Woo, Remote Patient Monitoring Service Through World-Wide Web, Proceedings—19th International Conference—IEEE/EMBS, Oct. 30-Nov. 2, 1997, 928-931.

Betty L. Grundy, M.D., Pauline Crawford, R.N., Paul K. Jones, Ph.D., May Lou Kiley, Ph.D., Arnold Reisman, Ph.D., Yoh-Han Pao, Ph.D., Edward L. Wilkerson, M.D., J. S. Gravenstein, M.D., Telemedicine in Critical Care: An Experiment in Health Care Delivery, Oct. 1977, 6:10.

Betty Lou Grundy, M.D., Paul K. Jones, Ph.D., and Ann Lovitt, M.D., Telemedicine in Critical Care: Problems in Design, Implementation, and Assessment, Critical Care Medicine, Jul. 1982, vol. 10, No. 7, 471-475.

Geraldine Fitzpatrick, TARDIS Evaluation: Report on Final Usage Evaluation of the TARDIS Telehealth System, Jul. 24, 1998, Issue No. 1.0.

ABSTRACT Marie Delima, R.N., M. Michael Shabot, M.D., FACS, FCCM, FACMI, Karen Morris, R.N, Janet Mould, R.N., Eden Torre-Javier, R.N., Mark Lobue, B.A. and Jeannie Chen, Pharm.D., Successful Implementation of a Multiple-ICU Clinical Information System in a Tertiary Care Medical Center.

Xin Li, Daniel J. Valentino, George J. So, Robert Lufkin, Ricky K. Taira, A World Wide Web Telemedicine System, SPIE vol. 2711, 427-439.

Stephen M. Ayres, M.D., F.C.C.M., Ake Grenvik, M.D., Ph.D., F.C. C.M., Peter R. Holbrook, M.D., F.C.C.M., William C. Shoemaker, M.D., F.C.C.M., Textbook of Critical Care, 3rd Edition, 1995, Harcourt Brace & Company.

Karen B. Tate, Ph.D., Reed M. Gardner, Ph.D., Kurt Scherting, Nurses, Pagers, and Patient-Specific Criteria; Three Keys to Improved Critical Value Reporting, 1995, 164-168, AMIA, Inc.

Karen E. Tate, Ph.D., Reed M. Gardner, Ph.D., Computers, Quality, and the Clinical Laboratory: A Look at Critical Value Reporting, 17th Annual Symposium on Computer Applications in Medical Care, Oct. 30-Nov. 3, 1993, 193-197.

Peter J. Haug, Reed M. Gardner, Karen E. Tate, R. Scott Evans, Thomas D. East, Gilad Kuperman, T. Allan Pryor, Stanley M. Huff, and Homer R. Warner, Decision Support in Medicine: Examples from the HELP System, Computers and Biomedical Research 27, 1994, 396-418.

Thomas D. East, Ph.D., C. Jane Wallace, R.N., M.S., Alan H. Morris, M.D., Reed M. Gardner, Ph.D., and Dwayne R. Westenskow, Ph.D., Computers in Critical Care, New Technologies in Critical Care, Jun. 1995, vol. 7, No. 2, 203-216.

Reed M. Gardner, Ph.D., Bette B. Maack, R.R.A., R. Scott Evans, Ph.D., and Stanley M. Huff, M.D., Computerized Medical Care: The HELP System at LDS Hospital, Journal of AHIMA, Jun. 1992, 63(6):68-78.

Reed M. Gardner, Ph.D., Integrated Computerized Records Provide Improved Quality of Care with Little Loss of Privacy, Journal of the AMIA, Jul./Aug. 1994, vol. 1, No. 4, 320-322.

S Reddy, M Niewiadomska-Bugaj, Y V Reddy, H C Galfalvy, V Jagannathan, R Raman, K. Srinivas, R. Shank, T. Davis, S. Friedman, MD, B. Merkin, MD, M. Kilkenny,MD, Experience with ARTEMIS—An Internet-Based Telemedicine System, AMIA, 1997, 759-763.

Patrick R. Norris, M.S., Benoit M Dawant, Ph.D., Antoine Geissbuhler, M.D., Web-Based Data Integration and Annotation in the Intensive Care Unit, 1997.

H. C. Galfalvy, M.S., S. M. Reddy, Ph.D., M. Niewiadomska-Bugaj, Ph.D., S. Friedman, M.D., Evaluation of Community Care Network (CNN) System in a Rural Heatlth Care Setting, 1995, AMIA Inc., 698-702.

K. Major, M. Shabot, S. Cunneen, Wireless Critical Alerts and Patient Outcomes in the Surgical Intensive Care Unit; The American Surgeon, 2000; p. 1057-1060.

M. Shabot, M. Lobue, Cedars-Sinai Medical Center Critical Alerting System, Feb. 2004; p. 1-16.

Shabot MM, LoBue M, Leyerle BJ, Dubin SB. Inferencing strategies for automated ALERTS on critically abnormal laboratory and blood gas data, SCAMC 1989; 13:54-57.

APACHE® III Equation Update (Version III-J) 2002, pp. 1-22.

APACHE® III Equation Update (Version III-I) 2003, pp. 1-13.

O. Kostopoulau, M. Wildman, Sources of Variability in Uncertain Medical Decisions In the ICU: A Process Tracing Study, Qual. Saf. Health Care 2004, 13:272-280.

A. Seiver, Critical Care Computing: Past, Present, and Future; Critical Care Clinics, vol. 16, No. 4, Oct. 2000, pp. 1-17.

J. Fisher, S. Harbarth, A. Agthe, A. Benn, S. Ringer, D. Goldmann, and S. Fancani, Quantifying Uncertainty: Physicians' Estimates of Infection in Critically Ill Neonates and Children; Clinical Infection Diseases 2004:38, pp. 1383-1390.

N. Halpern, S. Pastores, R. Greenstein, Critical Care Medicine in the United States 1985-2000: An Analysis of Bed Numbers, Use, and Cost; Critical Care Medicine 2004, vol. 32, No. 6, pp. 1254-1259.

J.Mrus, Getting Beyond Diagnostic Accuracy: Moving Toward Approaches That Can Be Used in Practice; Clinical Infectious Diseases 2004:38, pp. 1391-1393.

B. Leyerle, M. Shabot, Integrated Computerized Databases for Medical Data Management Beyond the Bedside, International Journal of Clinical Monitoring and Clinical Computing 1990:7, pp. 83-89.

M.Shabot, M. Lobue, B. Leyerle, S. Dubin, Decision Support Alerts For Clinical Laboratory and Blood Gas Data, Int. J. Clinical Monitoring and Computing 1990:7, pp. 27-31.

M. Shabot, M. Lobue, Real-Time Wireless Decision Support Alerts on a Palmtop PDA; Proc. Ann. Symp. Compt Appl. Med Care 1995, pp. 174-179.

G. Kuperman, D. Sittig, M. Shabot, J.Teich, Clinical Decision Support for Hospital and Critical Care, pp. 174-179.

W. Bates, M. Cohen, L. Leape, J. Overhage, M. Shabot, T. Sheridan, Reducing the Frequency of Errors In Medicine, J. American Medical Informatics Assn. 2001:8 pp. 299-308.

M. Shabot, B. Leyerle, M. Lobue, Automatic Extraction of Intensity Intervention Scores From A Computerized Surgical ICU Flowsheet, Am. J. Surg 1987:154:1, pp. 72-76.

Terry Ann Capuano, et al., Remote Telemetry, Nursing Management, Vo. 26, No. 7, Jul. 1995.

Valeriy Nenov and John Klopp, Remote Access to Neurosurgical ICU Physiological Data using the World Wide web, health Care in the Information Age, 1996, pp. 242-249.

Betty L. Grundy, et al., Telemedicine in Critical Care: An Experiment in Health Care Delivery, JACEP, vol. 6, Oct. 1977, pp. 439-444.

Susan L. Mabry, et al., Integrated Medical Analysis System, Proceedings of the 1997 Winter Simlation Conferece,, 1997, pp. 1163-1168.

Simon M. Kaplan and Geraldine Fitzpatrick, Designing Support for Remote Intensive-Care Telehealth Using the Locales Framework, ACM, 1997, pp. 173-184.

Douglas A. Perednia, Telemedine Technology and Clinical Applications, JAMA, vol. 6, Feb. 8, 1995.

Silvia Miksch,Artificial Intelligence for Decision Support: Needs, Possibilities, and Limitations in ICU, 10th Postgraduate Cousre in Critical Care Medicine A.P.I.C.E. '95, Springer, 1995, pp. 1-11.

Ho Sung Lee, et al., Remote Patient Monitoring Service through World-Wide Web, Proceedings—19th International Conference-IEEE/EMBS Oct. 30-Nov. 2, 1997 Chicago, IL. USA.

Doctors use 'remote control' to monitor ICU patients, CNN.com. technology>computing, Aug. 21, 2000, http://www.cnn.com/2000/TECH/computing/08/21/icu.t_t/index.html.

Finding Value in Intensive Care, From Afar, The New York Times on the Web, Jul. 27, 1999, www.Visicu.com/press/news/storyItem117.html.

Remote Monitoring of ICU Patients Lowers Mortality Rates, Complications, Johns Hopkins Newsrelease, Mar. 20, 2001, http://www.newswire.com/p/articles/view/23099/.

Brian A. Rosenfeld, M.D., FCCM, FCCP, et al., Intensive care unit telemedicine: Alternate paradigm for providing continuous intensivist care, Critical Care Medicine, vol. 28, No. 12, 2000 p. 3925-3931.

Benjamin Berg, Dale Vincent, and Donald Hudson, Remote Critical Care Consultation: Telehealth Projection of Clinical Specialty Expertise, Tripler Army Medical Center, Honolulu.

Xin Li, et al., A World Wide Web Telemedicine System, SPIE vol. 2711 p. 427-439.

Guidelines for Intensive Care Unit Design, Critical Care Medicine, Mar. 1995; 23(3):582-588.

Michael Breslow, et al., Effect of a Multiple-Site Intensive Care Unit Telemedicine Program on clinical and Economic Outcomes: An Alternative Paradigm for Intensivist Staffing, Critical Care Medicine 2004 vol. 32, No. 1.

Richard Brilli, et al., Critical care Delivery in the Intensive Care Unit: Defining Clinical Roles and the Best Practice Model, Critical Care Medicine 2001 vol. 29, No. 10.

M. Michael Shabot, et al., Decision Support Systems in Critical Care, 1994, Springer-Verlag Publishing, New York.

Rosenfeld, et al. Intensive care unit telemedicine: alternate paradigm for providing continuous intensivist care, Dec. 28, 2000, www.ncbi.nlm.nih.gov.

Definitions of Intensive Care Unit (ICU) on the Web, Apr. 2004, www.google.com and other websites.

Grundy, Betty Lou; Jones, Paul; Lovitt, Ann; "Telemedicine in critical care: Problems in design, implementation and assessment" Jul. 1982. Critical Care Medicine vol. 10, No. 7.

Heterington, Laurel Traynowicz; "High tech meets high tough: telemedicine's contribution to patient wellness"; Spring, 1998; Nursing Administration Quarterly, vol. 22, No. 3.

Tsien, C.L. and Fackler, J.C., "Poor prognosis for existing monitors in the intensive care unit," Critical Care Medical Journal, vol. 25, No. 4 (1997) (p. 614-619).

Tsien, C.L. "Reducing False Alarms in the Intensive Care Unit: A Systematic Comparison of Four Algorithms," Proceedings Annual AMIA Fall Symposium (1997).

Kohane, I.S. and Halmowitz, I.J., "Hypothesis-Driven Data Abstraction with Trend Templates," Proceedings Annual AMIA Symposium on Computer Applications in Medical Care (1994), (p. 444-448).

Angus, D.C., et al. "Caring for the critically ill patient. Current and projected workforce requirements for care of the critically ill and patients with pulmonary disease: can we meet the requirements of an aging population?" (abstract) JAMA. Dec. 6, 2000; 284(21): 2762-70.

Celi, Leo Anthony, et al. "The eICU: It's Not Just Telemedicine." Crit. Care Med. 2001, vol. 29, No. 8 (Suppl.).

Hanson, C.W. 3rd, et al. "Effects of an organized critical care service on outcomes and resource utilization: a cohort study." (abstract) Crit. Care Med. Feb. 1999; 27(2):270-4.

Manthous, C.A., et al. "Effects of a medical intensivist on patient care in a community teaching hospital." (abstract) Mayo Clin. Proc. May 1997; 72(5):391-9.

Pronovost, P.J., et al. "Organizational characteristics of intensive care units related to outcomes of abdominal aortic surgery." (abstract) JAMA. Apr. 14, 1999; 281(14):1310-7.

Pronovost, Peter J., et al. "Physician Staffing Patterns and Clinical Outcomes in Critically Ill Patients: A Systematic Review." JAMA. Nov. 6, 2002; 288(17):2151-62.

"Remote Control." Modern Healthcare, Feb. 25, 2002 (4 pages).

Breslow, Michael J., et al. "Technology Strategies to Improve ICU Practice." Seminars in Anesthesia 24: 59-70, 2005.

Breslow, Michael J. "Remote ICU Care Programs: Current Status." J. Crit. Care: 22, 66-76, 2007.

Tsien, Christine L., "TrendFinder: Automated Detection of Alarmable Trends", Department of Electrical Engineering and Computer Science, Massachusetts Institute of Technology, Massachusetts; Jun. 2000.

Hosseinzadeh, Abolfazl, "A Rule-Based System for Vital Sign Monitoring in Intensive Care", Department of Electrical Engineering, McGill University, Montreal; Nov. 1993.

Aukburg, S.J. et al., "Automation of Physiological Data Presentation and Alarms in the Post Anesthesia Care Unit." In Symposium on Computer Applications in Medical Care, Nov. 5-8, 1989, Washington, DC; pp. 580-582.

Benis, A. M. et al., "Improved Detection of Adverse Cardiovascular Trends with the Use of a Two-Variable Computer Alarm" *Critical Care Medicine*, vol. 8, No. 2, Jun. 1980: 341-344.

Bierman, M. 1. et al., "Pulse Oximetry in the Postoperative Care of Cardiac Surgical Patients; A Randomized Controlled Trial." *Chest*, vol. 102, No. 5, Nov. 1992: 1367-1370.

Bradshaw, K. E., "Computerized Alerting System Warns of Life-Threatening Events." In Symposium on Computer Application in Medical Care, Oct. 25-26, 1986, Washington, DC; pp. 403-409.

Chizeck, H. J., "Modeling, Simulation and Control in a Data Rich Environment." In Symposium on Computer Applications in Medical Care, Oct. 25-26, 1986, Washington, DC; pp. 65-69.

Coiera, E., "Intelligent Monitoring and Control of Dynamic Physiological Systems." *Artificial Intelligence in Medicine*, vol. 5, 1993: pp. 1-8.

Colvin, J. R. et al., "Microcomputer-Controlled Administration of Vasodilators Following Cardiac Surgery: Technical Considerations." *J. Cardiothoracic Anesthesia*, vol. 3, No. 1, Feb. 1989: pp. 10-15.

Coplin, W. M. et al., "Accuracy of Continuous Jugular Bulb Oximetry in the Intensive Care Unit." Neurosurgery, vol. 42, No. 3, Mar. 1998: 533-540.

Crew, A. D. et al., "Preliminary Clinical Trials of a Computer-Based Cardiac Arrest Alarm." Intensive Care Med, vol. 17, 1991: 359-364.

Garfinkel, D. et al., "PONI: An Intelligent Alarm System for Respiratory and Circulation Management in the Operating Rooms." In Symposium on Computer Applications in Medical Care, Nov. 6-9, 1988, Washington, DC; pp. 13-17.

Garfinkel D. et al., "Patient Monitoring in the Operating Room: Validation of Instrument Reading by Artificial Intelligence Methods." In Symposium on Computer Applications in Medical Care, Nov. 5-8, 1989, Washington, DC; pp. 575-579.

Guedes de Oliveira, P. et al., "The Role of Computer Based Techniques in Patient Monitoring: Technical Note." *Acta Neuorchir*, vol. 55, 1992 (Suppl.): 18-20.

Hahnel, J. et al., "Can a Clinician Predict the Technical Equipment a Patient will Need During Intensive Care Unit Treatment? An Approach to Standardize and Redesign the Intensive Care Unit Workstation." J *Clinical Monitoring*, vol. 8, No. 1, Jan. 1992: 1-6.

Hall, G. L. & P.B. Colditz, "Continuous Physiological Monitoring: An Integrated System for Use in Neonatal Intensive Care." *Australian Physical & Engineering Sciences in Medicine*, vol. 18, No. 3, 1995; 139-142.

Hayes-Roth, B. et al., "Guardian: An Experimental System for Intelligent ICU Monitoring." In Symposium on Computer Applications in Medical Care, Nov. 5-9, 1994, Washington, DC; p. 1004.

Irazuzta, Jose, "Monitoring in Pediatric Intensive Care." *Indian J. Pediatrics*, vol. 60, 1993: 55-65.

Jans, R. et al., "A Low Cost ECG Central Station for Intensive Care." *Australian Physical & Engineering Sciences in Medicine*, vol. 13, No. 1, 1990: 31-35.

Jastremski, M. et al., "A Model for Technology Assessment as Applied to Closed Loop Infusion Sytems" *Critical Care Medicine*, vol. 23, No. 10, Oct. 1995: 1745-1755.

Klass, M. A. & E. Y. Cheng, "Early Response to Pulse Oximetry Alarms with Telemetry." *J. Clinical Monitoring*, vol. 10, No. 3, May 1994: 178-180.

Koski, E. M. J. et al., "A Knowledge-Based Alarm System for Monitoring Cardiac Operated Patients—Assessment of Clinical Performance." *International J Clinical Monitoring and Computing*, vol. 11, 1994: 79-83.

Koski, E. M. J. et al., "Development of an Expert System for Haemodynamic Monitoring: Computerized Symbolism of On-Line Monitoring Data." *International J. Clinical Monitoring and Computing*, vol. 8, 1992: 289-293.

Laffel, G. et al., "Using Control Charts to Analyze Serial Patient-Related Data." *Quality Management in Health Care*, vol. 3, No. 1, Fall 1994: 70-77.

L'Estrange, P. R. et al., "A Microcomputer System for Physiological Data Collection and Analysis." *Australian Dental Journal*, vol. 3 8, No. 5, Oct. 1993: 400-405.

M. de Beer, N. A. et al., "Clinical Evaluation of a Method for Automatic Detection and Removal of Artifacts in Auditory Evoked Potential Monitoring." J *Clinical Monitoring*, vol. 11, No. 6, Nov. 1995: 381-391.

Makivirta, A. et al., "The Median Filter as a Preprocessor for a Patient Monitor Limit Alarm System in Intensive Care." *Computer Methods and Programs in Biomedicine*, vol. 34, No. 2/3, Feb./Mar. 1991: 139-144.

Makivirta, A. & E. M. J. Koski, "Alarm-Inducing Variability in Cardiac Postoperative Data and the Effects of Prealarm Delay." Critical Care Medicine, vol. 8, No. 6, May 1994: 153-162.

Martin, J. F., "Closed-Loop Control of Arterial Pressure During Cardiac Surgery." J *Clinical Monitoring*, vol. 8, No. 3, Jul. 1992: 252-253.

Meyer, C., "Visions of Tomorrow's ICU." *American J. Nursing*, Apr. 1993: 27-31.

Nenov, V. I. et al., "Computer Applications in the Intensive Care Unit." *Neurosurgery Clinics of North America*, vol. 5, No. 4, Oct. 1994: 811-827.

Nobel, J. J., "Physiologic Monitoring Systems, Acute Care." *Pediatric Emergency Care*, vol. 8, No. 4, Aug. 1992: 235-237.

Orr, J. A. & Westenskow, D. R., "A Breathing Circuit Alarm System Based on Neural Networks." *J. Clinical Monitoring*, vol. 10, No. 2, Mar. 1994: 101-109.

Pappert, D. et al., "Preliminary Evaluation of a New Continuous Intra-Arterial Blood Gas Monitoring Device." *Acta Anaesthesiologica Scandinavica*, Suppl. 107, vol. 39, 1995: 67-70.

Rampil, I. J., "Intelligent Detection of Artifact." *The Automated Anesthesia Record and Alarm Systems*, Chapter 17, 1987: 175-190.

Runciman, W. B. et al., "The Pulse Oximeter: Applications and Limitations—An Analysis of 2000 Incident Reports." *Anaesthesia and Intensive Care*, vol. 2 1, No. 5, Oct. 1993: 543-550.

Sailors, R. M., "A Model-Based Simulator for Testing Rule-Based Decision Support Systems for Mechanical Ventilation of ARDS Patients." In Symposium on Computer Applications in Medical Care, Nov. 5-9, 1994, Washington, DC; p. 1007.

Sanklecha, M., "The Pulse Oximeter." *Indian J. Pediatrics*, vol. 60, No. 3, 1993: 469-470.

Schnapp, L. M. & N. J. Cohen, "Pulse Oximetry; Uses and Abuses." *Chest*, vol. 98, No. 5, Nov. 1990: 1244-1250.

Simpson, R. L., "Automating the ICU: Facing the Realities." *Nursing Management*, vol. 23, No. 3, Mar. 1992: 24-26.

Sittig, D. F. & M. Factor, "Physiological Trend Detection and Artifact Rejection: A Parallel Implementation of a Multi-State Kalman Filtering Algorithm." In Symposium on Computer Applications in Medical Care, Nov. 5-8, 1989, Washington, DC; pp. 569-574.

Stoodley, K. D. C. et al., "Problems in the Development of a Computerized Ward Monitoring System for a Pediatric Intensive Care Unit." *International J Clinical Monitoring and Computing*, vol. 8, 1992: 281-287.

Sukavaara, T. et al., "A Knowledge-based Alarm System for Monitoring Cardiac Operated Patients—Technical Construction and Evaluation." *International J. Clinical Monitoring and Computing*, vol. 10, 1993: 117-126.

Szaflarski, N. L., "Emerging Technology in Critical Care: Continuous Intra-Arterial Blood Gas Monitoring." *American J. Critical Care*, vol. 5, No. 1, Jan. 1996: 55-65.

Uckun, S., "Intelligent Systems in Patient Monitoring and Therapy Management." *International J. Clinical Monitoring and Computing*, vol. 11, 1994: 241-253.

Webb, R. K., "Medical Decision Making and Decision Analysis." *Anesthesia and Intensive Care*, vol. 16, No. 1, Feb. 1988: 107-109.

Yien, H. et al., "Spectral Analysis of Systemic Arterial Pressure and Heart Rate Signals as a Prognostic Tool for the Prediction of Patient Outcome in the Intensive Care Unit." *Critical Care Medicine*, vol. 25, No. 2, 1997: 258-266.

Tsien, Christine L. and James Fackler, "Poor Prognosis for Existing Monitors in the Intensive Care Unit" *Critical Care Medicine*, vol. 25, No. 4, 1997: 614-619.

Tsien, Christine L.. "Reducing False Alarms in the Intensive Care Unit: A Systematic Comparison of Four Algorithms" Proceedings *AMIA* Symposium, 1997. pp. 9-14 (unnumbered).

Tsien, Christine L. "Reducing False Alarms in the Intensive Care Unit: A Systematic Comparison of Four Algorithms" Proceedings Annual *AMIA* Fall Symposium (1997), p. 894.

Tsien, Christine L. and James C. Fackler "An Annotated Data Collection System to Support Intelligent Analysis of Intensive Care Unit Data." Proceedings of the Second International Symposium on Advances in Intelligent Data Analysis, Reasoning about Data; Aug. 4-6, 1997; X. Liu, P. R. Cohen, and M. R. Berthold, Eds.; Springer-Verlag, London, UK; pp. 111-121.

Zhao, Ruilin, "A Model-Based Expert System for Interpretation of Hemodynamic Data from ICU Patients." Department of Electrical Engineering and Computer Science, Massachusetts Institute of Technology; May 18, 1997 (pp. 1-121).

Cantrell, Mark. "Nurses Keep Watch from miles away or at the bedside." Nursing Spectrum, Jan. 2005 (4 pages).

eSearch™ Analysis and Reporting, Unlocking the eCareManager™ System, eICU® Program (4 pages). Based on its contents, we believe this was distributed in 2006.

eCareManager™ v3.5, Executive Summary, eICU® Program (copyright 2006, VISICU, Inc.) (4 pages).

eCareManager™ v3.5, Capsule Technologie's Device Connectivity Solution, eICU® Program (V.35.RN.25 Nov. 2006) (2 pages).

100% Ventilator Bundle Compliance Achieved with eICU® Program, eICU® Program (2 pages). Based on its contents, we believe this was distributed in 2006.

Nurses Frequently Asked Questions, eICU® Program (copyright 2006 VISICU, Inc.) (5 pages).

Smart Alert® Prompts, A Unique Early Warning System, eICU® Program (copyright 2006 VISICU, Inc.) (2 pages).

Hospital Administrators Frequently Asked Questions, eICU® Program (copyright 2006 VISICU, Inc.) (6 pages).

Federwisch, Anne. "From a Distance." NurseWeek, Jan. 9, 2006 (5 pages).

Physicians Frequently Asked Questions, eICU® Program (copyright 2006 VISICU, Inc.) (6 pages).

Summary of iMDSoft, LTD's Counterclaims—Filed Dec. 10, 2007.

Response to Summary of iMDSoft, LTD's Counterclaims—Filed Dec. 28, 2007.

* cited by examiner

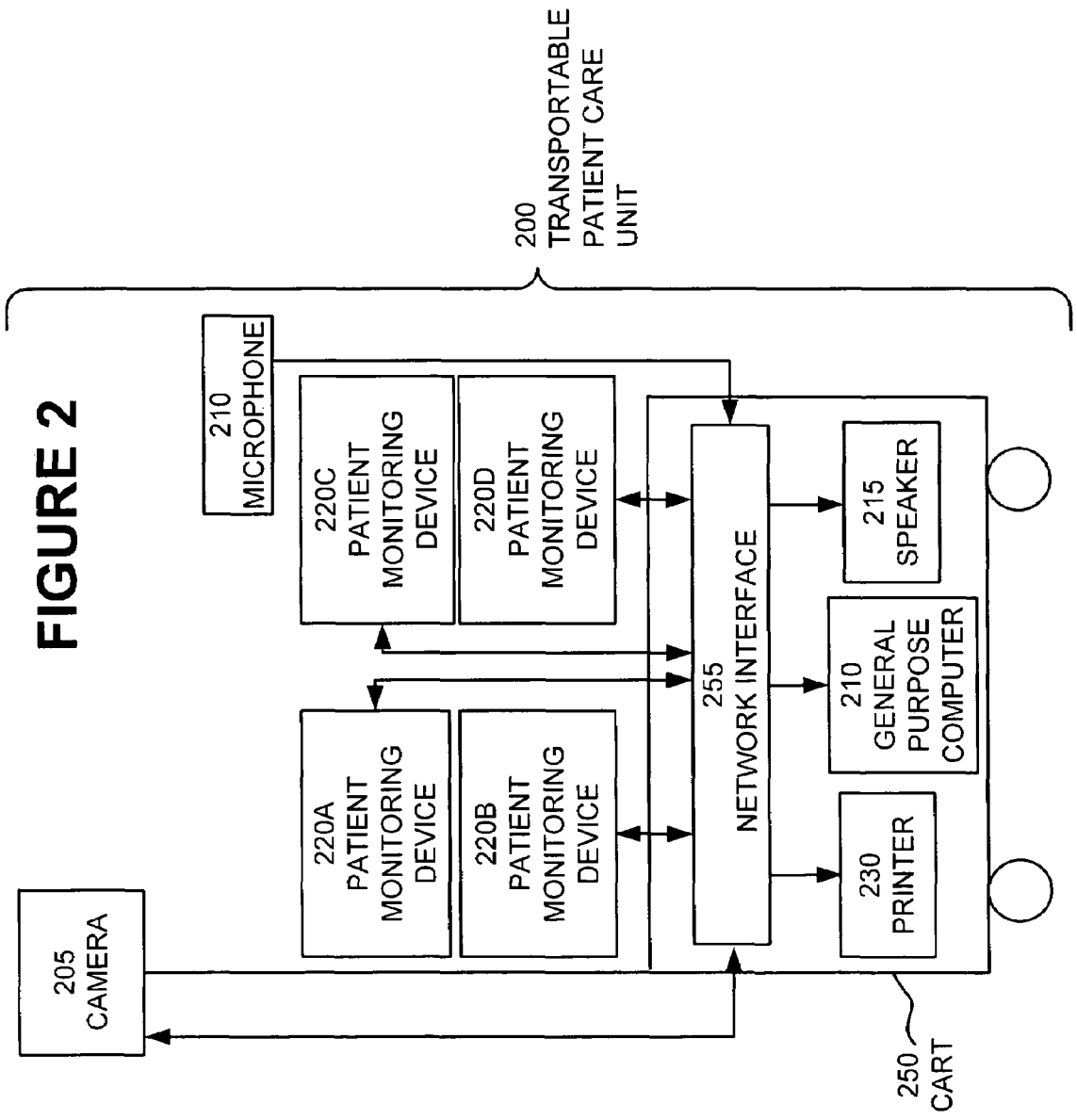

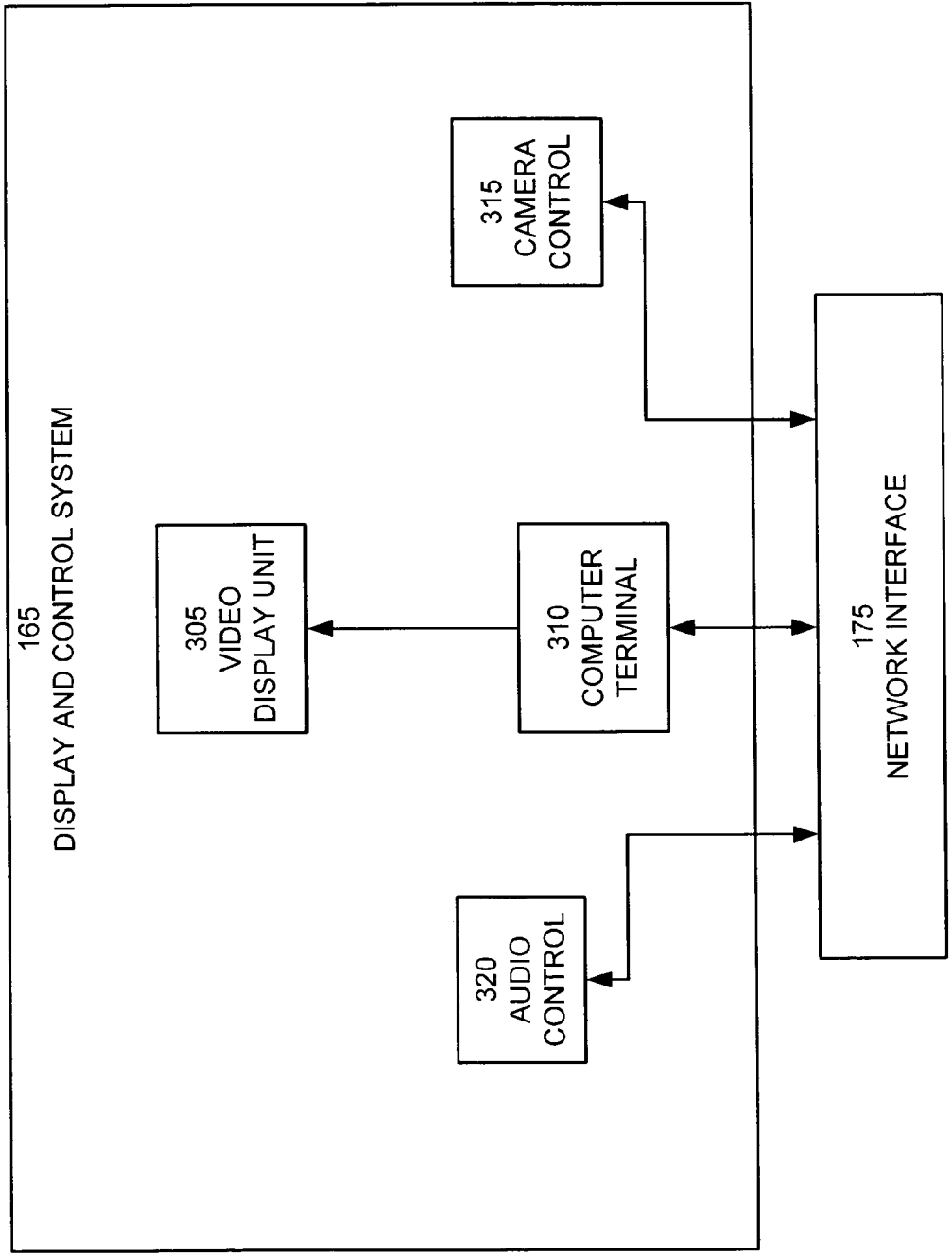

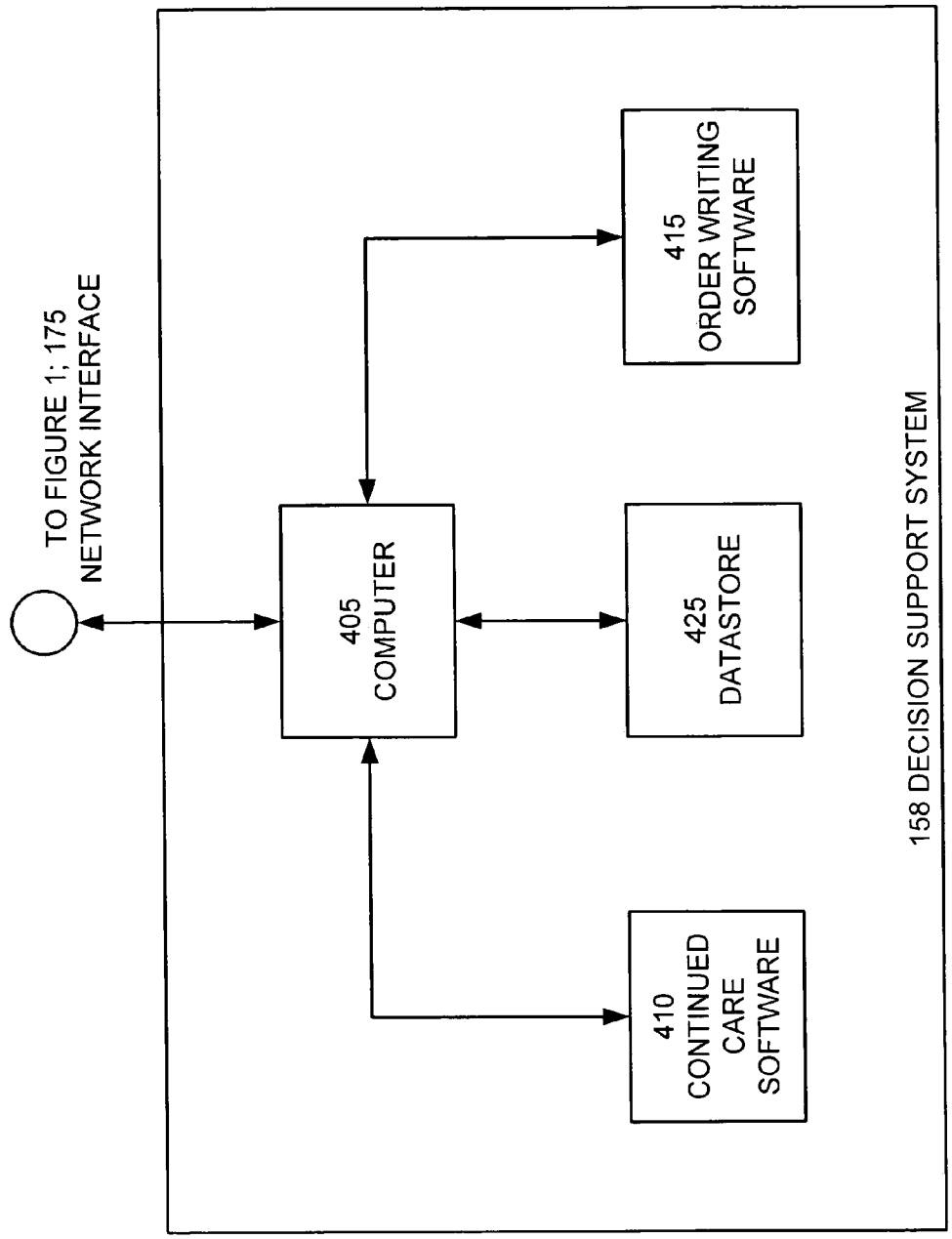

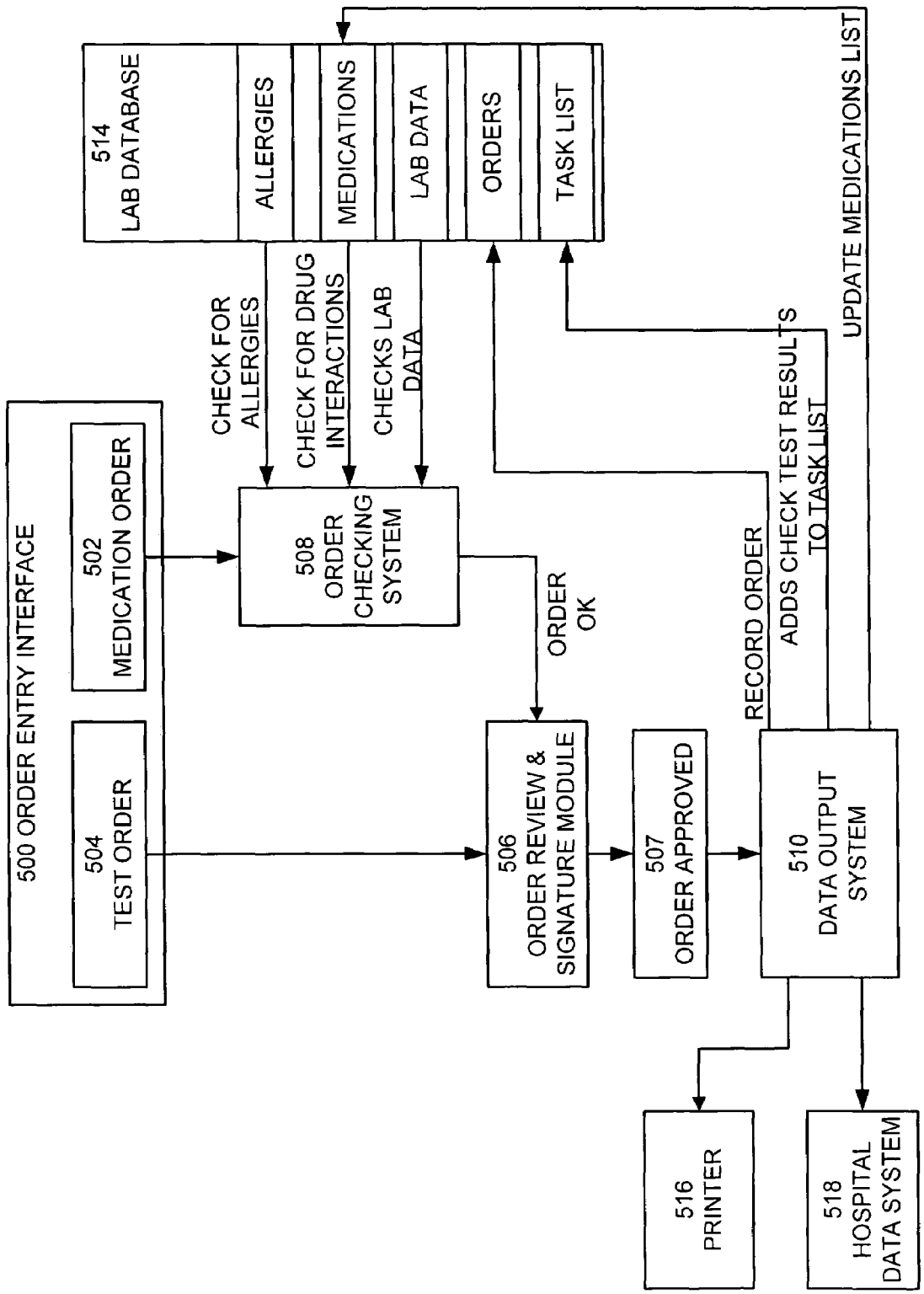

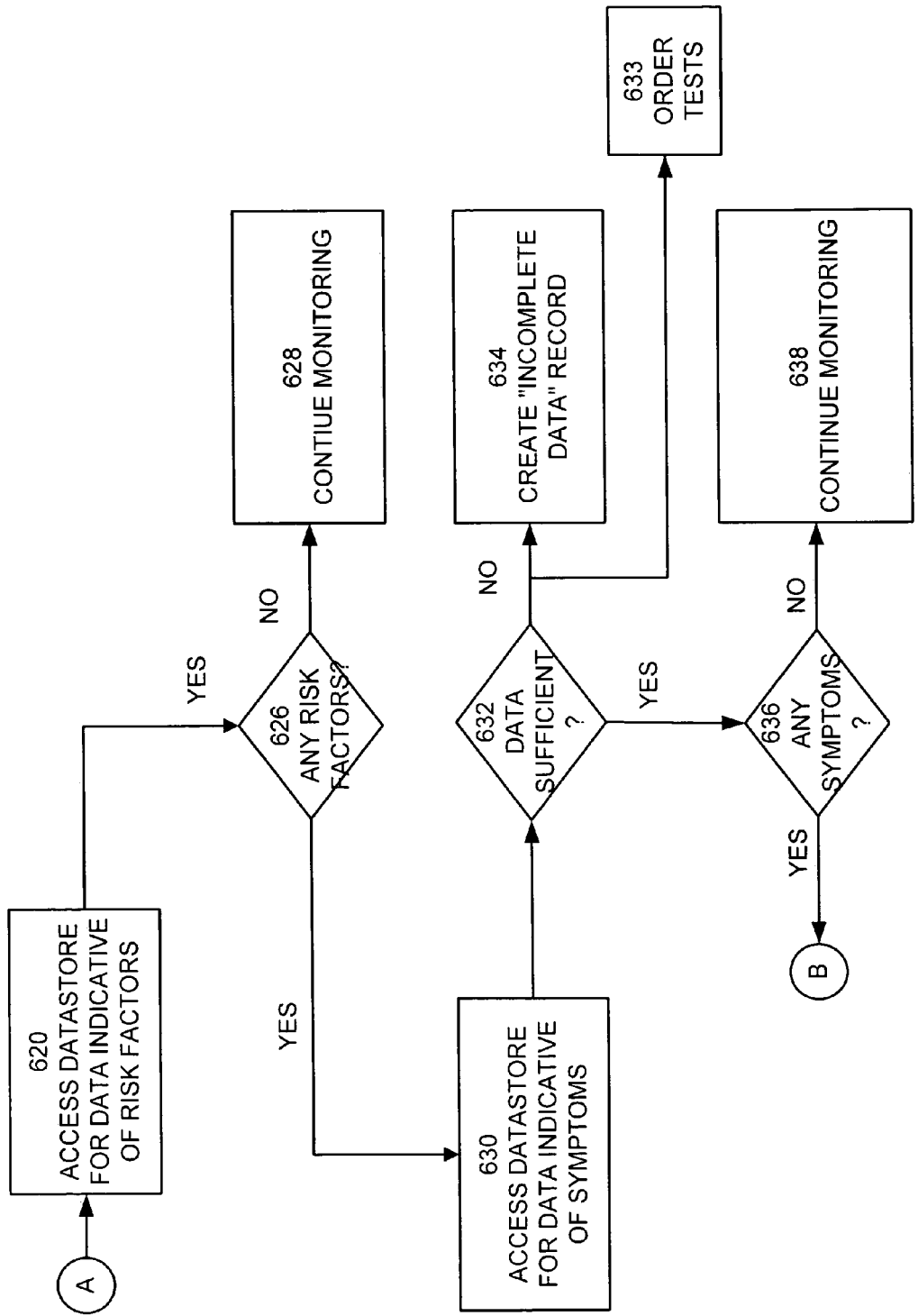

USING PREDICTIVE MODELS TO CONTINUOUSLY UPDATE A TREATMENT PLAN FOR A PATIENT IN A HEALTH CARE LOCATION

RELATIONSHIP TO OTHER APPLICATIONS

This application is a continuation in part of application Ser. No. 10/654,668 filed Sep. 4, 2003 and a continuation in part of application Ser. No. 10/946,548 filed Sep. 21, 2004, now U.S. Pat. No. 7,256,708 both of which are continuations-in-part of application Ser. No. 09/443,072 filed Nov. 18, 1999, now U.S. Pat. No. 6,804,656 issued Oct. 12, 2004, which claims the benefit of U.S. Provisional Application No. 60/141,520, filed Jun. 23, 1999. The Ser. Nos. 10/654,668, 10/946,548, 09/443,072, and the 60/141,520 applications are hereby incorporated by reference in their entirety for all purposes.

BACKGROUND

Embodiments of this invention relate generally to providing care to patients in healthcare locations. More particularly, embodiments of this invention provide a system and method for creating treatment plans for patients that are continuously updated based on patient data.

Advances in communications, video displays, monitoring devices and computers have made it possible to remotely monitor hundreds of monitored patients. Alerting systems may be deployed to alert healthcare providers when certain conditions are met. For example, in U.S. Pat. No. 5,942,986 issued to Shabot, et. al for a "System And Method For Automatic Critical Event Notification," describes a critical event notification system that permits review of a patient's diagnostic information, lab results, chart, or other data, automatically, by computer or similar equipment, and it provides for automatic paging of a responsible physician or physicians should a "critical event" be detected. The decision to page an individual is made automatically by the system, and does not require a direct human decision.

"Decision Support Systems in Critical Care" (Edited by M. Michael Shabot and Reed M. Gardner, 1994), is a compilation of articles that collectively describe the application of computers in health care settings. Decision support systems are defined as systems that receive medical data as input and produce medical information and/or knowledge as output. In some implementations, decision support systems utilize inferencing methods to detect associations between different pieces of information, alerting clinicians to certain patterns of events, which may be serious or life-threatening.

An example implementation of an inferencing method is described in the context of analyzing blood gas readings and laboratory results. Three different types of alerting algorithms are described: 1) high and low critical values 2) calculation-adjusted critical values, and 3) critical trends. (See, Decision Support Systems in Critical Care, pages 157-65.) The calculation-adjusted critical value algorithm reflects the dependence of the algorithm on multiple parameters. The application of the inferencing module produces an alert that is displayed on a screen or sent to a wireless device.

In U.S. Pat. No. 6,804,656 issued to Applicants, a smart alarm system was described. The smart alarm system of the '656 Patent, constantly monitors physiologic data and all other clinical information stored in the database (labs, medications, etc). The rules engine searches for patterns of data indicative of clinical deterioration. By way of illustration, one family of alarms looks for changes in vital signs over time, using pre-configured thresholds. These thresholds (also referred to as "rules") are patient-specific and setting/disease-specific. Physiologic alarms can be based on multiple variables. For example, one alarm looks for a simultaneous increase in heart rate of 25% and a decrease in blood pressure of 20%, occurring over a time interval of 2 hours. Alarms also track additional clinical data in the patient database. Other rules follow laboratory data (e.g. looking for need to exclude active bleeding and possibly to administer blood). Regardless of the data elements that are used, the purpose of the rules is to facilitate detection of changes in a patient's condition (whether that condition is improving or degrading) in a predictive manner and to automate a response appropriate to the "new" condition.

Clinical prediction has been practiced in various forms since the first doctor practiced medicine. Observation, intuition, and the prevailing wisdom of the time were used to diagnose and treat illness. The patient's status following a particular treatment was associated with the treatment, whether or not there was a causal connection between the two. Often, treatments that were ineffective, or worse, deleterious, were perpetuated because there was not basis for determining whether there was a cause and effect relationship between the treatment and the result.

Scoring systems were developed to identify the important physiologic parameters and chronic health conditions that determine clinical outcome. The typical clinical prediction rule is geared to determine a specific outcome. The identification of the key predictive variables is accomplished using well-known statistical techniques. The model is validated by applying the scoring system to patients and confirming the outcome against the predicted outcome.

An example of a predictive scoring system is the Acute Physiologic and Chronic Health Evaluation II (APACHE II) instrument commonly used to assess patients for admission to an ICU. The APACHE II instrument studied 5800 patients, and 13 hospitals, and, with statistical methods, identified 12 continuous physiologic variables measured within twenty-four hours of ICU admission." These variables were coupled with others describing the chronic health of the patient. APACHE II has also been applied to a wide variety of clinical issues in critical care and has been the method of choice for describing the severity of illness in some landmark studies.

APACHE II has several unintended flaws. The first was that the derivation data set was relatively small and therefore did not have the statistical power to describe subsets of disease, such as congestive heart failure, liver failure, and hematologic malignancy. The second was that the instrument could not distinguish between patients who had prior treatment and those who did not. This flaw, now termed "lead-term bias," was discovered when a number of investigators demonstrated that the predictive accuracy of APACHE II faltered when it was applied to patients who were transferred from other ICUs or from within the hospital setting. In these situations, the APACHE II instrument underestimated mortality.

APACHE III was intended to correct this deficiency. This instrument was derived from 17,440 patients, and 40 hospitals, representing a wider spectrum than APACHE II. APACHE III employs 17 continuous physiologic variables, chronic health information, prior treatment location before ICU admission, and principal ICU diagnosis. It also has a new feature whereby mortality prediction is updated on a continuous basis.

A Simplified Acute Physiologic Score (SAPS) was developed to streamline the approach utilized by the APACHE systems. The SAPS II system employs 17 variables: 12 categorical physiologic variables; age; type of admission; and three other designated disease variables (acquired immunodeficiency syndrome or AIDS, metastatic cancer, and hematologic malignancy). The SAPS score is entered into a mathematical formula, which can be solved on a calculator and whose solution provides the predicted hospital mortality. Therefore no commercial computer software is necessary to perform this calculation. This simplicity plus its low cost have made SAPS a popular choice in some centers, particularly in Europe.

The Mortality Prediction Model (MPM).uses a mathematical formula whose solution provides a prediction of patient mortality. Typically, the MPM score is determined immediately upon ICU admission. The updated version of MPM (MPM24) uses a score twenty-four hours after ICU admission, utilizing five of the admission variables and eight additional physiologic variables. This provides two points of prognostic assessment within a 24-hour period. The MPM24 correlates with SAPS and APACHE, since all three are measured within twenty-four hours of ICU admission.

Many other predictive models have been developed for various purposes. By way of illustration and not as a limitation, a partial list of predictive models comprises SAPS II expanded and predicted mortality, SAPS II and predicted mortality, APACHE II and predicted mortality, SOFA (Sequential Organ Failure Assessment), MODS (Multiple Organ Dysfunction Score), ODIN (Organ Dysfunctions and/or INfection), MPM (Mortality Probability Model), MPM II LODS (Logistic Organ Dysfunction System), TRIOS (Three days Recalibrated ICU Outcome Score), EUROSCORE (cardiac surgery), ONTARIO (cardiac surgery), Parsonnet score (cardiac surgery), System 97 score (cardiac surgery), QMMI score (coronary surgery), Early mortality risk in redocoronary artery surgery, MPM for cancer patients, POSSUM (Physiologic and Operative Severity Score for the enUmeration of Mortality and Morbidity) (surgery, any), Portsmouth POSSUM (surgery, any), IRISS score: graft failure after lung transplantation, Glasgow Coma Score, ISS (Injury Severity Score), RTS (Revised Trauma Score), TRISS (Trauma Injury Severity Score), ASCOT (A Severity Characterization Of Trauma), 24 h—ICU Trauma Score, TISS (Therapeutic Intervention Scoring System), TISS-28 (simplified TISS), PRISM (Pediatric RISk of Mortality), P-MODS (Pediatric Multiple Organ Dysfunction Score), DORA (Dynamic Objective Risk Assesment), PELOD (Pediatric Logistic Organ Dysfunction), PIM II (Paediatric Index of Mortality II), PIM (Paediatric Index of Mortality), CRIB II (Clinical Risk Index for Babies), CRIB (Clinical Risk Index for Babies), SNAP (Score for Neonatal Acute Physiology), SNAP-PE (SNAP Perinatal Extension), SNAP II and SNAPPE II, MSSS (Meningococcal Septic Shock Score), GMSPS (Glasgow Meningococcal Septicaemia Prognostic Score), Rotterdam Score (meningococcal septic shock), Children's Coma Score (Raimondi), Paediatric Coma Scale (Simpson & Reilly), and Pediatric Trauma Score.

Predictive models are useful in establishing an initial treatment plan for a patient. Continuous assessment of patient specific rules can facilitate the implementation of the treatment plan. However, it would also desirable to monitor the progress of the patient using predictive models to evaluate the effectiveness of the treatment plan on a continuous basis and to revise the treatment plan and/or the patient specific rules accordingly.

SUMMARY

An embodiment of the present invention uses a predictive model to establish a treatment plan and uses the treatment plan to develop a patient-specific rule for a monitored patient a healthcare location. The patient-specific rule is continuously applied to patient data to determine whether the rule has been contravened. The predictive model is applied continuously to the patient data to determine whether to revise the treatment plan. If the treatment plan is revised, the patient-specific rule may also be revised.

As used herein, a healthcare location may be a remote clinic, a doctor's office, a field hospital, a disaster aid station, a patient transport vehicle and similar care facilities. A patient may be selected for monitoring based on criteria established by the treatment facility. By way of illustration and not as a limitation, a "monitored patient" comprises a critically ill patient, an acutely ill patient, a patient with a specific illness, a patient with serious injuries, a surgical patient and a patient with an uncertain diagnosis.

Patient monitoring equipment acquires monitored data elements from a patient monitoring station and transmits the monitored data (sometimes also referred to herein as, "monitoring data") over a network to a remote command center. Monitored data comprises physiological data elements, video data elements, and audio data elements. The remote command center receives the monitored data from all patient monitoring stations. The remote command center also accesses other data relating to the condition of a patient. By way of illustration and not as limitation, the remote command center has access to data relating to personal information about the patient (name, address, marital status, age, gender, ethnicity, next of kin), medical history (illnesses, injuries, surgeries, allergies, medications), admissions information (symptoms, physiological data, time of admission, observations of admitting caregiver), treatment, lab data, test reports (radiology reports and microbiology reports for example), physician's notes, a patient's diagnosis, prescriptions, history, condition, laboratory results and other health-relevant data (collectively "patient data") to the extent available from the healthcare location. The data available to the remote command center over the network, that is, the monitored data and the patient data, is collectively referred to as "assessment data."

A rules engine applies a rule or rule set to the data elements selected from the assessment data from each monitored patient to determine whether the rule for that site has been contravened. In the event the rule has been contravened, an alert at the remote command center is triggered. Rules for each monitored patient may be established and changed at the remote command center for each as the patients' conditions warrant. In one embodiment of the present invention, a rule is established to determine whether a patient's condition is deteriorating. In another embodiment, a rule is established to determine whether a patient's condition is improving. In yet another embodiment of the present invention, an alert that a rule has been contravened comprises advice on treatment of the patient.

A patient rules generator establishes one or more rules for the monitored patient associated with a patient monitoring station. The rule is consistent with the treatment plan established for the patient. In an embodiment of the present invention, the patient rules generator collects rules performance measures indicative of the ability of the rule to predict changes in the condition of a patient and uses these measures to assess the efficacy of the rule. The patient rules generator may update a rule, determine that a rule is acceptable as is, or determine that there is insufficient data to revise a rule.

The patient rules generator may also evaluate the assessment data of patients with similar conditions to determine whether a predictive rule can be written and applied to patients with the same or similar conditions. The patient rules generator may also test a proposed rule against historical data to determine whether the rule is predictive of a change in a patient's condition.

In yet another embodiment of the present invention, the patient rules generator generates a rule that is consistent with the service level measures established by a site assessment module.

Another embodiment of the present invention provides continued care software that uses elements of the assessment data to provide decision support and that prompts a user for input to provide decision support to caregivers. A decision support algorithm responds to elements of assessment data to produce textural material describing a medical condition, scientific treatments and possible complications. This information is available in real time to assist in all types of clinical decisions from diagnosis to treatment to triage.

In still another embodiment of the present invention, order writing software facilitates the ordering of procedures and medications using patient-specific data. The order writing software and the continued care software are interactive allowing a caregiver to access features of both applications simultaneously, so that patient orders are given that are consistent and not conflicting with a patient's status and condition (i.e., allergies to medications or medications that may conflict with the order in question).

In an embodiment of the present invention, a healthcare location patient care system provides care to healthcare location patients based on the capabilities of the healthcare location. In this embodiment, the rules engine, the decision support algorithms, the order writing software facilities, and the continued care software are adapted to the capabilities of the healthcare location based on the application of site assessment rules to the healthcare location. In another embodiment of the present invention, components of a healthcare location patient care system may be supplied to the healthcare location to improve the level of its treatment capabilities. In still another embodiment of the present invention, components of the healthcare location are packaged and assigned a site assessment code. The code is used by the remote command center to predetermine elements of the site assessment process thereby simplifying that process.

In another embodiment of the present invention, patient monitoring equipment acquires monitored data elements from a patient monitoring station and stores monitoring data locally. The stored monitoring data is sent to a remote command center along with patient data at a pre-established time or when requested by remote command center. The remote command center evaluates the "delay" monitored data and assessment data in the same manner as if these data were received in real time. By way of illustration, the remote command center will apply the rules engine and the decision support algorithms to the delayed monitored data and patient data and provide guidance to the healthcare location. This embodiment of the present invention thus provides high quality care in environments where continuous high bandwidth communications are not available or economically infeasible.

In still another embodiment of the present invention, the delivery of stored monitoring data and patient data is expedited by an urgent consultation warning system (herein, the UCWS). The UCWS constantly evaluates the monitoring data and patient data before those data are stored to determine if an urgent consultation is warranted. By way of illustration and not as a limitation, changes in hemodynamic and respiratory measures over time indicative of a degrading condition of a patient would trigger an immediate reporting of all stored monitored and patient data to the remote command center for evaluation.

It is therefore an aspect of the present invention to receive at a remote command center monitoring data from a monitored patient over a communications network.

It is another aspect of the present invention to make available other data relating to the condition of a patient to the remote command center.

It is yet another aspect of the present invention to establish and/or revise rules at the remote command center and to apply a rules engine to "assessment data" to determine whether a rule is contravened.

It is another aspect of the present invention to determine based on assessment data whether the condition of a monitored patient warrants revising a rule at the remote command center.

It is still another aspect of the present invention to issue an alert from the remote command center in the event a rule is contravened.

It is an aspect of the present invention to provide treatment information in an order for an intervention issued by the remote command center to a treatment facility where a monitored patient is receiving care.

It is a further aspect of the present invention to apply decision support algorithms to data relating to the condition of a patient to provide decision support to caregivers.

It is another aspect of the present invention to provide a video visitation system that allows a remote visitation participant to participate in a video/audio conferencing session with a patient and/or a local visitation participant.

It is yet another aspect of the present invention to periodically acquire rules performance measures and use those measures to assess the efficaciousness of a rule.

In an embodiment of the present invention, a system for determining a treatment plan for a patient comprises a network, a datastore accessible via the network, a decision support system connected to the network, a rules generator connected to the network, and a rules engine connected to the network. By way of illustration and not as a limitation, the network may be a wired network, a wireless network, a satellite network, a public switched telephone network, an IP network, a packet switched network, a cell phone network, a cable network, a coax network, and a hybrid fiber coax network.

The datastore comprises assessment data elements indicative of a medical condition associated with the patient. The decision support system comprises a software module adapted for continuously applying a predictive model to a first set of selected assessment data elements to produce current health measures for the patient, and utilizing the health measures to produce a treatment plan for the patient, wherein the treatment plan is continuously updated based on the current health measures. By way of illustration and not as a limitation, a predictive model may be an APACHE II algorithm, an APACHE III algorithm, a history of present illness (HPI) algorithm, a review of systems (ROS) algorithm, a past, family, and/or social history (PFSH) algorithm, a Sequential Organ Failure Assessment (SOFA) model, and a mortality prediction model (MPM) algorithm.

In another embodiment of the present invention, the predictive model comprises a guideline selected from the list consisting of Acalculous Cholecystitis, Acute Pancreatitis Algorithms, Acute Renal Failure-Diagnosis, Acute Renal Failure-Management & Treatment, Adrenal Insufficiency. Agitation and Anxiety, Depression & Withdrawal, Aminoglycoside Dosing and Therapeutic Monitoring, an Amphotericin-B Treatment Guidelines, Analgesia, Antibiotic Classification & Costs, Antibiograms Algorithm, Antibiotic associated Colitis Algorithm, ARDS: Hemodynamic Management, ARDS: Steroid Use, ARDS: Ventilator Strategies, Asthma, Bleeding Patient, Bloodstream Infections, Blunt Cardiac Injury, Bradyarrhythmias, Brain Death, Bronchodilator Use in Ventilator Patients, Bronchoscopy & Thoracentesis Guidelines, Candiduria, Cardiogenic Shock, CardioPulmonary Resuscitation Guideline, Catheter Related Septicemia, a Catheter Replacement Strategies, Cervical Cord Injury, Congestive Heart Failure, COPD Exacerbation & Treatment, CXR (Indications), Dealing with Difficult patients and families, Diabetic Ketoacidosis, Dialysis, Diuretic Use, Drug Changes with Renal Dysfunction, Emergency Cardiac Pacing, Endocarditis Diagnosis and Treatment, Endocarditis Prophylaxis, End of Life Decisions, Endotracheal Tubes & Tracheotomy, Ethical Guidelines, Febrile Neutropenia, FUO, Fluid Resuscitation, Guillain-Barre Syndrome, Heparin, Heparin-Induced Thrombocytopenia, Hepatic Encephalopathy, Hepatic Failure, HIV+Patient Infections, Hypercalcemia Diagnosis and Treatment, Hyperglycemia Insulin Treatment, Hyperkalemia: Etiology & Treatment, Hypernatremia: Etiology & Treatment, Hypertensive Crisis, Hypokalemia: Etiology & Treatment, Hyponatremia: Etiology & Treatment, Hypothermia, Identification of Cervical Cord Injury, Implantable Cardio-defibrillator, Intra-Aortic Balloon Device, Intracerebral Hemorrhage, Latex Allergy, Magnesium Administration, Management of Hypotension, Inotropes, Management of Patients with Ascites, Empiric Meningitis, Meningitis, a Myasthenia Gravis, Myocardial Infarction, Myocardial Infarction with left bundle branch block, Necrotizing Soft Tissue Infections, Neuromuscular Blockers, Neuromuscular Complications of Critical Illness, Non-Infectious Causes of Fever, Non-Traumatic Coma, Noninvasive Modes of Ventilation, Nutritional Management, Obstetrical Complication, Oliguria, Open Fractures, Ophthalmic Infections, Organ Procurement Guidelines, PA Catheter Guideline and Troubleshooting, Pancreatitis, Penetrating Abdominal Injury, Penetrating Chest Injury, Penicillin Allergy, Permanent Pacemaker and Indications, Pneumonia Community Acquired, Pneumonia Hospital Acquired, Post-Op Bleeding, Post-Op Hypertension, Post-Op Management of Abdominal Post-Op Management of Carotid, Post-Op Management of Open Heart, Post-Op Management of Thoracotomy, Post-Op Myocardial Ischemia (Non-Cardiac Arrhythmias after Cardiac.Surgery), Post-Op Power Weaning, Pressure Ulcers, Pulmonary Embolism Diagnosis, Pulmonary Embolism Treatment, Respiratory Isolation, Sedation, Seizure, Status Epilepticus, Stroke, Sub-Arachnoid Hemorrhage, Supra-Ventricular Tachyarrhythmia, Supra-Ventricular Tachycardia, Wide Complex QRS Tachycardia, Therapeutic Drug Monitoring, Thrombocytopenia, Thrombolytic Therapy, Transfusion Guidelines, Traumatic Brain Injury, Assessment of Sedation, Sedation, Septic Shock, Bolus Sliding, Scale Midazolam, Short Term Sedation Process, Sinusitis, SIRS, Spinal Cord Injury, Steroid Replacement Strategy, Thyroid Disease, Transplant Infection Prophylaxis, Transplant Related Infections, Treatment of Airway Obstruction, Unknown Poisoning, Unstable Angina, Upper GI Bleeding Stress Prophylaxis, Vancomycin, Upper GI Bleeding Non-Variceal, Upper GI Bleeding Variceal, Use of Hematopoietic Growth Factors, Ventilator Weaning, Ventilator Weaning Protocol, Venous Thrombosis Diagnosis and Treatment, Venous Thromboembolism Prophylaxis, Ventricular Arrhythmia, Warfarin, Warfarin Dosing, and Wound Healing Strategies.

The rules generator is adapted for establishing a patient-specific rule consistent with the treatment plan for the patient. The rules engine is adapted for applying the patient specific rule to a second set of selected assessment data elements, determining whether the patient-specific rule for the patient has been contravened, and issuing an alert if the patient-specific rule for the patient has been contravened. In another embodiment of the present invention, the patient specific rule is applied continuously. In yet another embodiment of the present invention, the alert comprises an instruction to revise the treatment plan. In still an embodiment of the present invention, the alert comprises a patient intervention protocol and order.

In another embodiment of the present invention, the decision support system, the rules generator and rules engine are located within a command center and the patient is located at a healthcare location that is remote from the command center. In yet another embodiment of the present invention, the command center is adapted for monitoring a plurality of patients in a plurality of geographically dispersed health cared locations 24 hours per day 7 days per week.

In an embodiment of the present invention, the current health measures are indicative of applying medical treatment resources to the patient. In this embodiment, the treatment plan comprises applying medical treatment resources to the patient consistent with the medical condition.

In another embodiment of the present invention, the current health measures are indicative of denying medical treatment resources-to the patient. In this embodiment, the treatment plan comprises treating the patient consistent with standards of medical ethics.

In still another embodiment of the present invention, the current health measures are indicative of denying medical treatment resources to the patient. In this embodiment, the treatment plan is modified to withhold further medical treatment resources from the patient and to treat the patient consistent with standards of medical ethics.

In an embodiment of the present invention, the patient-specific rule for the patient comprises an algorithm.

In various embodiments of the present invention, the second set of selected data elements comprise: a physiological data element of the patient and a clinical data element of the patient, a physiological data element of the patient and a medication data element of the patient, a physiological data element of the patient and a laboratory data element of the patient, a clinical data element of the patient and a laboratory data element of the patient, and a physiological data element of the patient and another physiological data element of the patient.

In another embodiment of the present invention, the second set of selected data elements comprise at least two data elements of the patient selected from the group consisting of a physiological data element, a clinical data element of the patient, a medication data element of the patient, and a laboratory data element of the patient.

In an embodiment of the present invention, the rules engine is further adapted for determining whether the patient requires monitoring by the remote command center, and issuing a stop monitoring order in the event the patient does not require monitoring by the remote command center.

DESCRIPTION OF THE FIGURES

FIG. 2 illustrates the components of a transportable patient care unit according to embodiments of the present invention.

FIG. 3 illustrates a display and control system according to an embodiment of the present invention.

FIG. 4 illustrates a decision support system according to an embodiment of the present invention.

FIG. 5 illustrates an order writing data flow according to an embodiment of the present invention.

DETAILED DESCRIPTION

Figure 1:
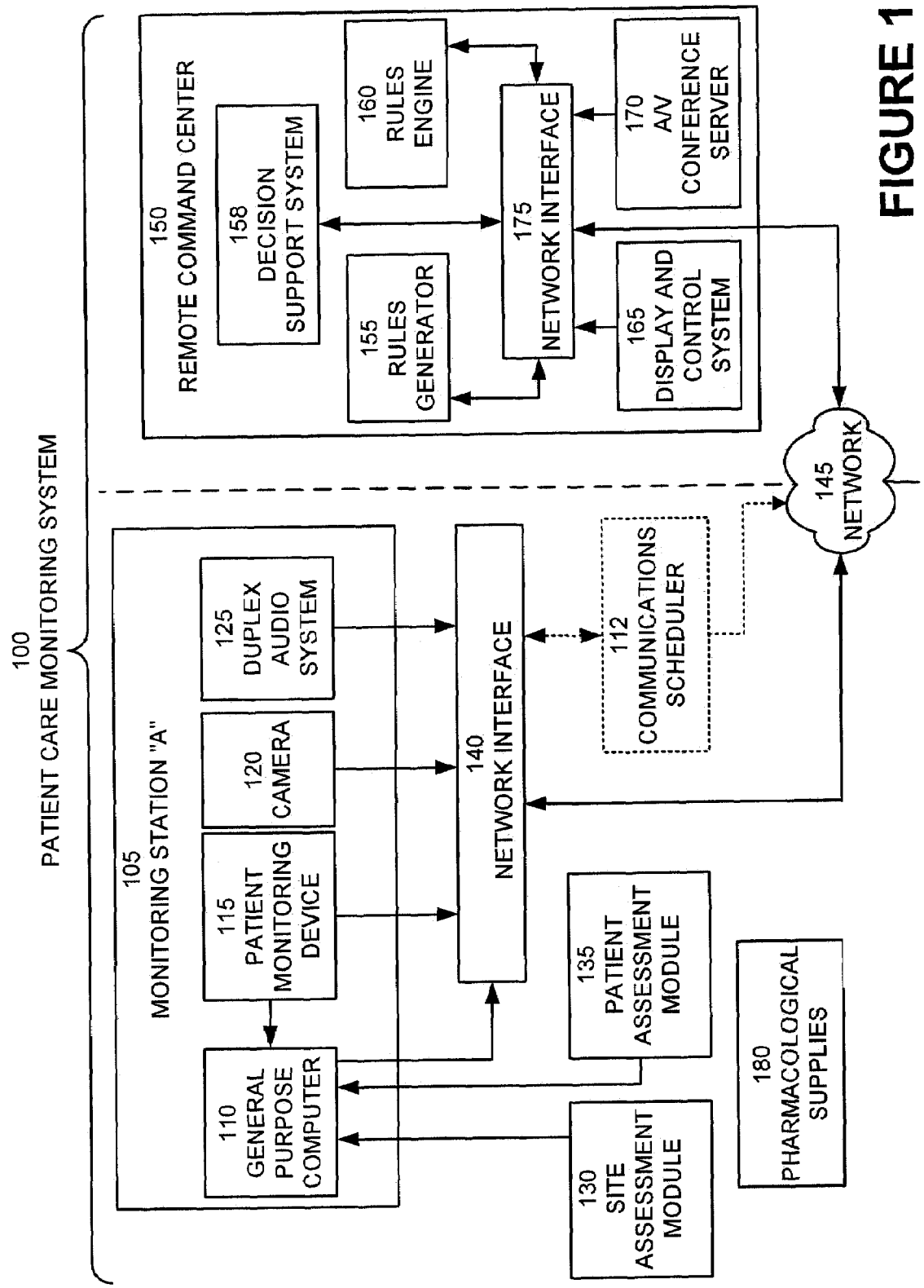
FIG. 1 illustrates a block diagram of the components of a monitored patient care system according to embodiments of the present invention.

The following terms used in the description that follows. The definitions are provided for clarity of understanding:

| | |
|---|---|
| assessment data | assessment data is all data relevant to the health of a patient. |
| healthcare location | A "healthcare location;" a facility, whether temporary or permanent, that is not generally equipped to provide expert medical care on a twenty-four basis. By way of illustration and not as a limitation, a healthcare location may be a remote clinic, a doctor's office, a field hospital, a disaster aid station, a patient transport vehicle and similar care facilities |
| caregiver | an individual providing care to a patient. Examples include a nurse, a doctor, medical specialist (for example and without limitation an intensivist, cardiologist or other similar medical specialist). |
| clinical data | data relating to the observed symptoms of a medical condition. |
| monitored patient | a person admitted to a healthcare location. |
| monitored data | data received from monitoring devices connected to a monitored patient. |
| monitored patient | a monitored patient from whom monitored data is collected and whose condition is subject to continuous real-time assessment from a remote command center. |
| patient data | data relating to a patient's diagnosis, prescriptions, history, condition, laboratory results and other health-relevant data. |
| physiological data | any data relating to the functions of the human body and its processes. |
| symptom | any sign or indication of a health condition that can be identified from patient reports and/or assessment data. |

An embodiment of the present invention uses a predictive model to establish a treatment plan and uses the treatment plan to develop a patient-specific rule for a monitored patient a healthcare location. The patient-specific rule is continuously applied to patient data to determine whether the rule has been contravened. The predictive model is applied continuously to the patient data to determine whether to revise the treatment plan. If the treatment plan is revised, the patient-specific rule may also be revised.

As used herein, a healthcare location may be a remote clinic, a doctor's office, a field, hospital, a disaster aid station, a patient transport vehicle and similar care facilities. A patient may be selected for monitoring based on criteria established by the treatment facility. By way of illustration and not as a limitation, a "monitored patient" comprises a critically ill patient, an acutely ill patient, a patient with a specific illness, a patient with serious injuries, and a patient with an uncertain diagnosis.

Patient monitoring equipment acquires monitored data elements from a patient monitoring station and transmits the monitoring data over a network to a remote command center. Monitored data comprises physiological data elements, video data elements, and audio data elements. The remote command center receives the monitoring data from all patient monitoring stations. The remote command center also accesses other data relating to the condition of a patient. By way of illustration and not as limitation, the remote command center has access to data relating to personal information about the patient (name, address, marital status, age, gender, ethnicity, next of kin), medical history (illnesses, injuries, surgeries, allergies, medications), admissions information (symptoms, physiological data, time of admission, observations of admitting caregiver), treatment, lab data, test reports (radiology reports and microbiology reports for example), physician's notes, a patient's diagnosis, prescriptions, history, condition, laboratory results and other health-relevant data (collectively "patient data") to the extent available from the healthcare location. The data available to the remote command center over the network, that is, the monitoring data and the patient data, is collectively referred to as "assessment data."

In an embodiment of the present invention, a monitored patient care system provides care to monitored patients based on the capabilities of the healthcare location. In this embodiment, the rules engine, the decision support algorithms, the order writing software facilities, and the continued care software are adapted to the capabilities of the healthcare location based on the application of site assessment rules to the healthcare location. In another embodiment of the present invention, components of a healthcare location patient care system may be supplied to the healthcare location to improve the level of its treatment capabilities. In still another embodiment of the present invention, components of the healthcare location are packaged and assigned a site assessment code. The code is used by the remote command center to predetermine elements of the site assessment process thereby simplifying that process.

FIG. 1 illustrates a block diagram of the components of a monitored patient care system according to embodiments of the present invention. A monitored patient care system 100 comprises patient monitoring station "A" 105. While FIG. 1 illustrates a single patient monitoring station, the invention is not so limited. Multiple patient monitoring stations may be used without departing from the scope of the present invention. For the sake of clarity, the description that follows will refer to patient monitoring station "A" 105. However, the description applies to all patient monitoring stations within the monitored patient care system 100.

Patient monitoring station "A" 105 comprises a general purpose computer 110, a patient monitoring device 115, a camera 120, and a duplex audio system 125. While FIG. 1 illustrates a patient monitoring device, the invention is not so limited. Multiple patient monitoring devices may be used without departing from the scope of the present invention. For the sake of clarity, the description that follows will refer to patient monitoring 115.

General purpose computer 110 provides data entry, display and printing capabilities through means known to those skilled in the art.

As will be appreciated by those skilled in the art, monitoring station "A" 105 may be portable without departing from the scope of the present invention. In an embodiment of the present invention, monitoring station "A" 105 is integrated into a patient supporting device, as for example and not as a limitation, a bed, a gurney, or a wheelchair. Monitoring station "A" 105 may also be assembled on a cart or other mobile structure.

The components of patient monitoring station "A" 105 are connected to network 145 via network interface 140. Network 145 may be a wired network, a wireless network, a satellite network, a public switched telephone network, an IP network, a packet switched network, a cell phone network, a cable network, and a coax network, a hybrid fiber coax network.

Pharmacological supplies 180 comprise an inventory of medicines that is provided to a healthcare location depending on circumstances. By way of illustration and not as a limitation, a monitored patient care system 100 may be operated in a full service hospital facility or dropped shipped to a disaster area where the primary concern is sanitation-based illnesses. In the former instance, the full service hospital would have access to all available medications. However, in the case of the drop shipped field hospital, pharmacological supplies 180 would comprise those medications, diagnostic tools, and preventive agents that are useful in countering the expected diseases and not readily available to the healthcare location. In contrast, if the disaster area is most likely to experience patients with physical injuries, pharmacological supplies would be weighted to supplies needed to diagnose, treat, and comfort the wounded.

An optional site assessment module 130 and an optional patient assessment module 135 connect to network interface 140 via general purpose computer 110. It is anticipated that a monitored patient care system 100 equipped with the optional site assessment module 130 and the optional patient assessment module 135 will be used in healthcare locations that have limited resources. Site assessment module 130 provides information indicative of the ability of a healthcare location to provide diagnostic, laboratory, surgical, and pharmacological services. In an embodiment of the present invention, the site assessment module acquires data from the healthcare location produces service level measures comprising an inventory of available monitoring data elements, an inventory of available diagnostic services, an inventory of available surgical treatment services, and an inventory of available laboratory services. These data may be acquired via a survey or by reference to a database in which the survey data of the healthcare location are stored. Alternatively, in another embodiment of the present invention, a monitored patient care system comprises an assessment code that details the capability of the monitored patient care system 100. By way of illustration and not as a limitation, the assessment code may indicate the number of monitoring devices incorporated into the monitored patient care system 100, the patient parameters that can be acquired using the monitoring devices, and the pharmacological supplies 180 provided with the monitored patient care system 100.

Optional patient assessment module 135 provides patient condition data indicative of a monitored patient to remote command center 150. In an embodiment of the present invention, patient assessment module 135 acquires data relating to a patient's diagnosis, prescriptions, history, condition, laboratory results and other health-relevant data. These data may be acquired via a survey, or by reference to a database in which the patient condition data are stored.

As will appreciated by those skilled in the art, site assessment module 130 and a patient assessment module 135 may be standalone components or may be software applications operating on general purpose computer 110.

Also connected to network 145 is remote command center 150. Remote command center 150 comprises a patient rules generator 155, a rules engine 160, decision support system 155, display and control system 165, and audio/video (A/V) conferencing server 170. Decision support system 158 issues instructions to the rules generator 155 when rules required for a patient. Once the rules are generated by rules generator 155, the decision support system 158 causes the rule to be referred to the rules engine 160 for subsequent application to the specific patient for whom the rule was originally generated. A network interface 175 provides connectivity between network 145 and the other elements of the remote command center. Network 145 is configured to permit access to external networks (not illustrated), such as the Internet.

Video camera 120 is movable both horizontally and vertically and zoomable through remote commands from the display and control system 165 of remote command center 150 so that specific views of the patient may be obtained both up close and generally. Duplex audio system 125 comprises a speaker and microphone (not illustrated) to permit both one-way audio monitoring of the patient and two-way communication with the patient or others in proximity to patient monitoring station "A" 105.

Patient monitoring device 115 acquires physiological data from a patient in real-time. In an embodiment of the present invention, general purpose computer 110 comprises a printer that receives and prints orders and instructions from an authorized remote caregiver. By way of illustration and not as a limitation, an order comprises a lab order, a medication, and a procedure. Orders are tailored to the capabilities of the healthcare location patient care system 100.

A network interface 140 provides access to network 145 for transmission of the monitored data, video signal, and audio signals to the remote command center 125 and the receipt of the audio signals and, optionally, printer signals at the monitoring station.

FIG. 2 illustrates the components of a transportable patient care unit according to embodiments of the present invention. A transportable patient care unit 200 comprises the components illustrated in FIG. 1 mounted on a cart 250. Video camera 205 is movable both horizontally and vertically and zoomable through remote commands from the display and control system 165 of remote command center 150 (see, FIG. 1) so that specific views of the patient may be obtained both up close and generally. A microphone 210 and a speaker 215 permit both one-way audio monitoring of the patient and two-way communication with the patient or others located in proximity to transportable patient care unit 200. Patient monitoring devices 220A-220D acquire physiological data from a patient in real-time. A printer 230 receives and print orders from an authorized caregiver. By way of illustration and not as a limitation, an order comprises a lab order, a medication, and a procedure. A network interface 255 provides access to a network (see FIG. 1, 150) for transmission of the monitored data, video signal, and audio signals to a remote command center and the receipt of the audio signals and printer signals at the monitoring station. A general purpose computer 210 allows on site care givers to provide additional data that may be germane to the care of the patient.

Referring again to FIG. 1, the remote command center 125 receives monitored data from patient monitoring station "A" 105 and patient condition data from patient assessment module 135 via network 145 through network interface 175. Monitored data comprises real-time data received from monitoring equipment at patient monitoring station "A" 105 that is configured to receive physiological data monitored patient and associated with patient monitoring station "A" 105.

The rules generator 155 and the rules engine 160 facilitate detection of impending problems and automate problem detection thereby allowing for intervention before a patient condition reaches a crisis state. Rules engine generator 155 establishes one or more rules for the monitored patient associated with patient monitoring station "A" 105. In an embodiment of the present invention, rules generator 155 generates a rule that is consistent with the patient assessment data and with the service level measures established by the site assessment module 130. The rules engine 160 continuously applies a rule to selected data elements of patient assessment data (assessment data is all data relevant to the health of a patient) to determine whether the rule for a monitored patient has been contravened. In the event the rule has been contravened, the remote command center issues an alert.

In one embodiment of the present invention, a rule is established to determine whether a patient's condition is deteriorating and an alert comprises an intervention order and protocol. In another embodiment of the present invention, the rules engine is further adapted to determine whether a monitored patient requires monitoring by a monitoring station. If not, a release protocol and order are issued. In still another embodiment of the present invention, a rule dictates threshold limits for changes over time of specific vital sign data. Thresholds that are patient-specific disease-specific are established. The rules engine then evaluates the monitored data for the specific vital sign data to determine if a change threshold has been exceeded.

For example, a patient with coronary artery disease can develop myocardial ischemia with relatively minor increases in heart rate. Heart rate thresholds for patients with active ischemia (e.g. those with unstable angina in a coronary care unit) are set to detect an absolute heart rate of 75 beats per minute. In contrast, patients with a history of coronary artery disease in a surgical ICU have thresholds set to detect either an absolute heart rate of 95 beats per minute or a 20% increase in heart rate over the baseline. For this threshold, current heart rate, calculated each minute based on the median value over the preceding 5 minutes, is compared each minute to the baseline value (the median value over the preceding 4 hours).

In another embodiment of the present invention, a rule is based on multiple variables. By way of illustration, a rule is contravened if the rules engine determines that monitored data reflects both a simultaneous increase in heart rate of 25% and a decrease in blood pressure of 20%, occurring over a time interval of 2 hours.

For multi-variable rules, thresholds rely on known or learned associations between changes in multiple variables, which variables may comprise diverse data types. Thus, a rule may associate monitored physiological data with patient clinical data. The association may change depending on the diagnosis of the patient, the medication given the patient, and the results of laboratory data. For example, a rule may associate central venous pressure and urine output, because simultaneous decreases in these two variables can indicate that a patient is developing hypovolemia. Another rule may cause the rules engine to evaluate laboratory data (e.g. looking for need to exclude active bleeding and possibly to administer blood).

In an embodiment of the present invention, a rule established for a monitored patient and the monitored patient is associated with a particular monitoring station. In this embodiment, if the patient were later associated with a different monitoring station, the remote command center would associate the rule with the different monitoring station at the time that the association between the monitored patient and the different monitoring station is made. In this way, rules "move" with the patient without manual intervention:

In another embodiment of the present invention, patient rules generator 155 establishes one or more rules for the monitored patient associated with patient monitoring station "A" 105. The patient rules generator 155 receives rules performance measures indicative of the ability of the rule to predict changes in the condition of a patient and uses these measures to assess the efficacy of the rule. By way of illustration and not as a limitation, the rules performance measures may be derived from survey data from healthcare professionals with experience with the rule or with the relationship of certain variables used by the rule to other variables or to a particular medical condition. Alternatively or in conjunction with survey data, the patient rules generator 155 may review historical data using multivariate analyses to relate variables, rules, and patient outcomes. By way of illustration and not as a limitation, the patient rules generator 155 may use ANOVA or BSS to automatically produce rules performance measures of existing rules and to identify new relationships among variables that may be used to form new rules. The patient rules generator 155 may update a rule, determine that a rule is acceptable as is, or determine that there is insufficient data to revise a rule.

The patient rules generator 155 may also evaluate the assessment data of patients with similar conditions to determine whether a predictive rule can be written and applied to patients with the same or similar conditions. The rules generator 155 may also test a proposed rule against historical data to determine whether the rule is predictive of a change in a patient's condition.

In yet another embodiment of the present invention, the patient rules generator 155 generates a rule that is consistent with the service level measures established by a site assessment module 130.

In another embodiment of the present invention, patient monitoring equipment acquires monitored data elements from a patient monitoring station and stores monitoring data in general purpose computer 110. The stored monitoring data is sent from general purpose computer 110 to the remote command center 150 along with patient data under control of an optional communications scheduler 112 at a pre-established time such as hour or when an "event" occurs as noted below, or when requested by remote command center 150. The remote command center 150 evaluates the "delayed" monitored data and assessment data in the same manner as if these data were received in real time. By way of illustration, the remote command center will generate rules using patient rules generator 155, apply those rules using rules engine 160 to the delayed monitored data and patient data and provide guidance to the monitored patient care system 100. The decision support algorithms of decision support system 158 may also be applied to the delayed monitored data and patient data. This embodiment of the present invention thus provides high quality care in environments where continuous high bandwidth communications are not available or economically infeasible.

In still another embodiment of the present invention, the delivery of stored monitoring data and patient data is expedited by an urgent consultation warning system (herein, the UCWS) operated by general purpose computer 110. The UCWS constantly evaluates the monitoring data and patient data before those data are stored to determine if an event has occurred that warrants an urgent consultation. By way of illustration and not as a limitation, changes in hemodynamic and respiratory measures over time indicative of a degrading condition of a patient would trigger an immediate reporting of all stored monitored and patient data to the remote command center 150 for evaluation.

Referring to FIG. 1, the display and control system 165 provides the human interface for the remote command center. FIG. 3 illustrates a display and control system according to an embodiment of the present invention. A display and control system 165 comprises a video display unit 305, a computer terminal 310, a camera control 315, and an audio control 320. The video display unit 305 displays real-time monitoring data and video images from patient monitoring station "A" 105.

The computer terminal 310 allows selecting the layout and content displayed on the video display unit 305, provides access to the record of the patient associated with patient monitoring station "A" 105, and permits entry of data into that record. The camera control 315 permits control from the remote command center 125 of the video camera 120 (see FIG. 1) at the patient monitoring station "A" 105. The audio control permits control from the remote command center 150 of a microphone and a speaker within the duplex audio system 125 of patient monitoring station "A" 105. Connectivity between the components of the display and control systems 165 and patient monitoring station "A" 105 is provided by network interface 175, network 145, and network interface 140.

Referring again to FIG. 1, the remote command center 150 comprises decision support system 158. FIG. 4 illustrates a decision support system according to an embodiment of the present invention. Referring to FIG. 4, decision support system 158 is connected to network interface 175 and comprises a computer 405. Computer 405 operates continued care software 420 and order writing software 415. Continued care software 410 and order writing software 415 make calls to datastore 425 to access the assessment data related to a particular monitored patient associated with patient monitoring station "A" 105 (see, FIG. 1).

Continued care software 420 comprises decision support algorithms that operate on elements of assessment data and/or input from a caregiver to facilitate decisions relating to diagnosis, treatment and triage. Continued care software may be applied at the time the patient is admitted and throughout the patient's stay within a treatment facility. Thus, a diagnosis may be made based on the initial data acquired during admission, following the completion of laboratory procedures, or after other pertinent information is acquired. In an embodiment of the present invention, continued care software 420 evaluates selected data elements of assessment data continuously and provides an alert if those data are indicative of a different diagnosis. The alert may take the form of suggested diagnoses that are vetted by a series of questions posed by the continued care software 420 to a caregiver. Based on the responses to the questions, a suggested diagnosis may be eliminated. The alert may also comprise instructions for specific tests to be run on the monitored patient to help formulate a new diagnosis. Once a diagnosis is confirmed, the continued care software 420 continues to monitor changes in patient data and issues an alert if the current diagnosis should be reevaluated by a caregiver.

Decision support system 158 also issues instructions to the rules generator 155 when rules required for a patient. Once the rules are generated by rules generator 155, the decision support system 158 causes the rule to be referred to the rules engine 160 for subsequent application to the specific patient for whom the rule was originally generated.

In another embodiment of the present invention, patient monitoring equipment acquires monitored data elements from a patient monitoring station and stores monitoring data in general purpose computer 110. The stored monitoring data is sent from general purpose computer 110 to the remote command center 150 along with patient data under control of an optional communications scheduler 112 at a pre-established time such as hour or when an "event" occurs as noted below, or when requested by remote command center 150. The continued care decision support system 158 evaluates selected data elements of the assessment data in the same manner as if these data were received in real time and provides an alert if those data are indicative of a different diagnosis.

In still another embodiment of the present invention, the delivery of stored monitoring data and patient data is expedited by an urgent consultation warning system (herein, the UCWS) operated by general purpose computer 110. The UCWS constantly evaluates the monitoring data and patient data before those data are stored to determine if an event has occurred that warrants an urgent consultation. By way of illustration and not as a limitation, changes in hemodynamic and respiratory measures over time indicative of a degrading condition of a patient would trigger an immediate reporting of all stored monitored and patient data to the decision support system 158 for evaluation.

In still another embodiment of the present invention, continued care software 420 operates on a diagnosis to "triage" a patient. For example and without limitation a caregiver requests an Apache II score based on the diagnosis. Continued care software 420 calls selected data elements from datastore 425 appropriate to the diagnosis. The values of the selected data elements are weighted according to an algorithm and a patient severity score is determined. This patient severity score is used to determine whether the patient is treated in a patient monitoring station. For example, if one embodiment of the present invention, if the severity score is greater than or equal to a particular threshold, the patient is identified as requiring observation via a patient monitoring station. If the severity score is less than that threshold, the patient is triaged to a facility other than a patient monitoring station, thereby assigning patient monitoring stations to patients who are most likely to benefit from monitoring and continued assessment.

Other scoring algorithms may be used without departing from the scope of the present invention. By way of illustration and not as a limitation, continued care software 420 may comprise algorithms to perform APACHE II, APACHE III, a history of present illness (HPI) score, a review of systems (ROS) score, a past, family, and/or social history (PFSH) score, SOFA (Sequential Organ Failure Assessment) score, and a mortality prediction model (MPM) score. The scoring results from one or more of these algorithms may be used to determine a treatment plan for the patient. As will be appreciated by those skilled in the art, a scoring result may be used to determine to apply resources to a patient that is determined to be a candidate for treatment consistent with the patient's medical condition or to withhold or discontinue the application of resources to a patient that is determined to be untreatable consistent with standards of medical ethics.

In yet another embodiment of the present invention, a patient is scored continuously based on patient assessment data that is accessed by the continued care software 420. A scoring algorithm or a collection of algorithms are applied to updated assessment data to determine whether the current treatment plan is viable or should be amended.

In another embodiment of the present invention, computer 405 operates order writing software 415, either independently or in conjunction with the operation of continued care software 420 to order tests to complete the data required for a potential diagnosis.

According to another embodiment of the present invention, the orders issued by order writing software 415 are consistent with the service level measures established by the site assessment module 130.

FIG. 5 illustrates an order writing data flow according to an embodiment of the present invention. Referring to FIG. 5, order entry user interface 500 allows the caregiver to order procedures and medication to assist the patients at a patient monitoring station. For example, the caregiver can order an ECG 504. Thereafter the order is reviewed and a digital signature relating to the caregiver is supplied 506. Once reviewed and signed off, the order is approved 507 and sent to the data output system 510. Thereafter the data output system prints the order to the printer at a patient monitoring station 516. For record keeping purposes the order is exported in the HL7 language to the hospital data system 518. In addition the data output system adds an item to the database that will subsequently cause a caregiver to check the ECG results. This notification to the task list is provided to the database 514. In addition, as part of the database an orders file relating to the specific patient is also kept. The fact that an ECG has been ordered is entered in the orders file for that patient.

The order entry functionality of the present invention provides a critical service for obtaining information on the patient during admission, medical orders, and procedures provided to the patient during the ICU stay. For example:

| | |
|---|---|
| Radiology: | Contains all radiology performed on a particular patient. |
| Radiology results: | Contains the results of each radiology test performed on the particular patient. |
| Drugs: | Contains all relevant information for all the drugs that a patient has been administered. |
| Laboratory: | Contains all laboratory tests ordered for a patient. |
| Microbiology result: | Contains the results of microbiology organisms taken on a patient. |
| Laboratory result: | Contains the results for a laboratory test ordered for a particular patient. |

In a similar fashion using the order entry user interface 500 the caregiver can order medications 502 for a patient.

According to an embodiment of the present invention, the order entry interface 500 uses an identification algorithm to facilitate order entry. As text is entered into the interface, suggested entry values are provided to the user for selection, thereby reducing the entry time and the opportunity of mistakes.

The medication order then is provided to an order checking system 508. The order checking system retrieves information from the database 514 relating to allergies of the patient and medication list that comprises medications that are already being administered to the patient. This allows for the order checking system to check for drug allergies and drug interactions. Further laboratory data is extracted from the database 514 and the order checking system checks to insure that there will be no adverse impact of the recommended dosage upon the renal function of the patient. Additionally, a patient with kidney and/or liver problems may have the dosage adjusted based on the slower excretion time for such patients. Once the order checking system 508 is completed, the order is approved and provided to the order review and signature module 506. In this module the digital signature of a caregiver is affixed to the order electronically and the order is approved 507. Thereafter it is provided to the data output system 510 where again the orders are printed or transmitted via HL7 for the patient monitoring station 516, for the pharmacy 517 and for the treatment facility data system 518. In this case, any medications that are ordered are then provided to the medications list file in the database 514 so that the complete list of all medications that are being administered to the patient is current.

In an embodiment of the present invention, order checking system 508 determines whether the order is consistent with the service level measures established by the site assessment module 130. If the order is not consistent with the service level measures, the order is suppressed and the caregiver is notified that an alternative treatment is required.

As noted, the order writing software 415 may also interact with continued care software 410. Referring again to FIG. 4, a caregiver selects a suggested diagnosis from the continued care software 420 and enters the order writing software 415. As previously described, the orders issued by order writing software 415 are consistent with the service level measures established by the site assessment module 130. The order writing software identifies the appropriate test or tests and issues the actual order or orders for the identified tests. Each order is then sent to the appropriate testing facility. The tests are conducted, and the completion of the order is reported to the data store 425 and the completion information is received by the order writing software 415. Additionally, continued care software 420 acquires the test results from the datastore 425 and updates the list of suggested diagnoses.

Continued care software 420 provides reference material directed to the standardized treatment of the monitored patient. In order to standardize treatment provided to monitored patients at the highest possible level, decision support algorithms are used in the present invention. These include textural material describing the topic, scientific treatments and possible complications. This information is available in real time to assist in all types of clinical decisions from diagnosis to treatment to triage.

In an embodiment of the present invention, the decision response algorithms are responsive to the service level measures established by the site assessment module 130. In this embodiment, the algorithms adjust the response to fit the capabilities of the healthcare location.

As noted earlier, an aspect of the present invention is to standardize care and treatment across patient monitoring stations. This is effective in the present invention by providing decision support to caregivers as well as information concerning the latest care and practice standards for any given condition. Table 1 below is an exemplary list of a wide variety of conditions within the general categories of cardiovascular, endocrinology, general, gastrointestinal, hematology, infectious diseases, neurology, pharmacology, pulmonary, renal, surgery, toxicology, for which algorithms of care have been developed. As will be appreciated by those skilled in the art, the list in Table 1 is not exhaustive and other decision support algorithms may be developed for other conditions without departing from the scope of the present invention.

TABLE 1

Bradyarrhythmias diagnosis & treatment
Cardiogenic shock treatment
Cardio-pulmonary resuscitation treatment
Congestive heart failure diagnosis & treatment
Emergency cardiac pacing indications
Fluid resuscitation indications & treatment
Hypertensive crisis treatment
Implantable cardio-defibrillators indications
Intra-aortic balloon devices indications
Magnesium treatment
Treatment of hypotension
Myocardial infarction diagnosis & treatment
MI with left bundle branch block diagnosis
Pulmonary artery catheter indications
Permanent pacemakers indications
Pulmonary embolism diagnosis
Pulmonary embolism treatment
Supra-ventricular tachyarrhythmias diagnosis & treatments
Unstable angina diagnosis & treatment
Venous thromboembolism prophylaxis treatment
Venous thrombosis: diagnosis & treatment
Ventricular arrhythmias diagnosis & treatment
Adrenal insufficiency diagnosis and treatment
Diabetic ketoacidosis diagnosis and treatment
Hypercalcemia: diagnosis & treatment

TABLE 1-continued

Hyperglycemia: insulin treatment
Steroid replacement treatment
Thyroid disease diagnosis and treatment
End of life treatment decisions
Pressure ulcers treatment
Organ procurement indications
Antibiotic associated colitis diagnosis and treatment
Hepatic encephalopathy diagnosis and treatment
Hepatic failure diagnosis and treatment
Treatment of patients with ascites
Nutritional management
Acute pancreatitis diagnosis and treatment
Upper gastro-intestinal bleeding: stress prophylaxis treatment
Upper gastro-intestinal bleeding: non-variceal treatment
Upper gastro-intestinal bleeding: variceal treatment
Heparin treatment
Heparin-induced thrombocytopenia diagnosis and treatment
The bleeding patient diagnosis and treatment
Thrombocytopenia diagnosis and treatment
Thrombolytic treatment
Transfusion indications
Hematopoetic growth factor indications
Warfarin treatment
Acalculus cholecystitis diagnosis and treatment
Bloodstream infections diagnosis and treatment
Candiduria diagnosis and treatment
Catheter related septicemia diagnosis and treatment
Catheter replacement strategies
Endocarditis prophylaxis
Endocarditis diagnosis and treatment
Febrile neutropenia diagnosis and treatment
Fever of Unknown Origin diagnosis
HIV+ patient infections diagnosis and treatment
Meningitis diagnosis and treatment
Necrotizing soft tissue infections diagnosis and treatment
Non-infectious causes of fever diagnosis
Ophthalmic infections diagnosis and treatment
Pneumonia, community acquired diagnosis and treatment
Pneumonia, hospital acquired diagnosis and treatment
Septic shock diagnosis and treatment
Sinusitis diagnosis and treatment
Systemic Inflammatory Response Syndrome diagnosis and treatment
Transplant infection prophylaxis
Transplant-related infections diagnosis and treatment
Agitation, anxiety, depression & withdrawal treatment
Brain death diagnosis
Guillain-barre syndrome diagnosis and treatment
Intracerebral hemorrhage diagnosis and treatment
Myasthenia gravis diagnosis and treatment
Neuromuscular complications of critical illness diagnosis and treatment
Non-traumatic coma diagnosis
Sedation treatment
Status epilepticus diagnosis and treatment
Stroke diagnosis and treatment
Sub-arachnoid hemorrhage diagnosis and treatment
Aminoglycoside dosing and therapeutic monitoring
Amphotericin-b treatment
Analgesia treatment
Drug changes with renal dysfunction
Penicillin allergy diagnosis and treatment
Neuromuscular blocker treatment
Vancomycin treatment
Adult Respiratory Distress Syndrome: hemodynamic treatment
Adult Respiratory Distress Syndrome: steroid treatment
Adult Respiratory Distress Syndrome: ventilator treatment
Asthma diagnosis & treatment
Bronchodilator use in ventilator patients
Bronchoscopy & thoracentesis indications
Chronic Obstructive Pulmonary Disease treatment
Chest X-ray indications
Noninvasive modes of ventilation indications
Endotracheal tubes & tracheotomy indications
Treatment of airway obstruction
Ventilator weaning
Acute renal failure: diagnosis and treatment
Dialysis indications
Diuretic treatment
Hyperkalemia: diagnosis & treatment
Hypernatremia: diagnosis & treatment

TABLE 1-continued

Figure 6A:
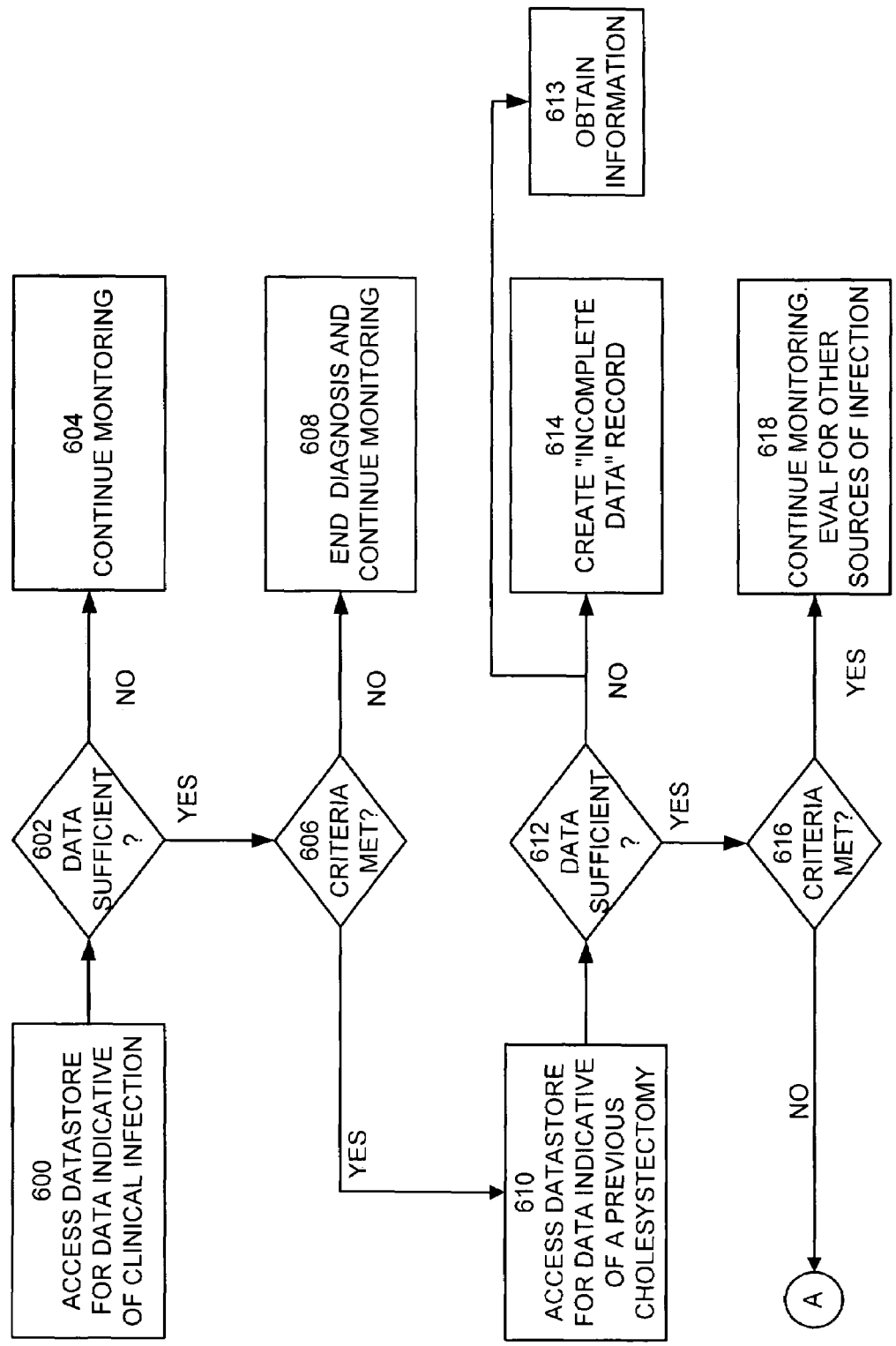
FIGS. 6A, B, C, and 6D illustrate the flow of a decision support algorithm for acalculous cholecsystitis according to an embodiment of the present invention.

Hypokalemia: diagnosis & treatment
Hyponatremia: diagnosis & treatment
Oliguria diagnosis and treatment
Obstetrical complications and treatment
Dissecting aortic aneurysm diagnosis and treatment
Post-operative hypertension treatment
Post-operative myocardial ischemia (non-cardiac surgery) treatment
Diagnosis and treatment of arrhythmias after cardiac surgery
Diagnosis and treatment of post-operative bleeding
Post-operative management of abdominal
Post-operative management of open heart
Post-operative management of thoracotomy
Post-operative management of carotid
Wound healing treatment
Diagnosis and treatment of acetaminophen overdose
Diagnosis and treatment of anaphylaxis
Diagnosis and treatment of cocaine toxicity
Diagnosis and treatment of alcohol withdrawal
Diagnosis and treatment of hyperthermia
Diagnosis and treatment of latex allergy
Diagnosis and treatment of unknown poisoning
Diagnosis and treatment of abdominal compartment syndrome
Diagnosis and treatment of blunt abdominal injury
Diagnosis and treatment of blunt aortic injury
Diagnosis and treatment of blunt cardiac injury
Deep Venous Thrombosis prophylaxis treatments
Acid-base disturbance diagnosis and treatment
Electrolyte disturbance diagnosis and treatment
Severity adjustment calculation and outcome prediction
Ventilator treatment
Continuous renal replacement treatment
Infusion pump administration treatment
Fungal infection diagnosis and treatment
Viral infection diagnosis and treatment
Diagnosis and treatment of extremity compartment syndrome
Diagnosis and treatment of head injury
Diagnosis and treatment of hypothermia
Diagnosis and treatment of identification of cervical cord injury
Diagnosis and treatment of spinal cord injury
Diagnosis and treatment of open fractures
Diagnosis and treatment of penetrating abdominal injury
Diagnosis and treatment of penetrating chest injury
Admission criteria
Discharge criteria
Patient triage
Discharge planning FIGS. 6A, B, C and 6D illustrate an application of a decision support algorithm for the diagnosis and treatment of acalculous cholecystitis to patient data according to an embodiment of the present invention. FIGS. 6A through 6D are exemplary only and are not limiting. As will be appreciated by those skilled in the art, decision support algorithms (DSAs) for other conditions may be implemented in the continued patient care software without departing from the scope of the present invention.

Referring to FIG. 6A, a datastore comprising patient data is accessed by the DSA 600 for data indicative of clinical infection. A determination is made whether the data is sufficient to determine whether the patient is clinically infected 602. If the data necessary to make the decision are not available, the system continues its monitoring 604 until data in the datastore indicates otherwise. Alternatively, an alert may be issued on a monitor at the command center although this is not a requirement for further tests to be ordered. Test that are ordered by the DSA are then performed on the patient to obtain the data required for the decision.

If the data are sufficient, a determination is made whether the patient meets criteria for a clinical infection as measured by elevated temperature and leukocystosis 606. In an embodiment of the present invention, the criteria are temperature great than 102 F., or a white blood cell count greater than 12,000. If the criteria for clinical infection are not met the system of the present invention goes back into its continuous monitoring mode 608. The process is then complete and the continuous monitoring of the present invention continues.

If the patient is clinically infected 606, the DSA accesses the patient data datastore and acquires data indicative of whether the patient has had a previous cholecystectomy 610. A determination is then made whether the data is sufficient to determine whether the patient has had a previous cholecsystectomy 612. If the data necessary to make the decision are not available, the DSA prompts the caregiver to find out this information 613. When the information is obtained it is put into the datastore. Notations of "incomplete data" are kept by the system so that treatment records and need for tests can be audited. This is accomplished by storing an "incomplete data" record 614.

If the data are sufficient, a determination is made whether the patient has had a previous cholecystectomy 616. If the patient has had a previous cholecystectomy, it is very unlikely that the patient has acalculous cholecystitis. Therefore the DSA has completed its analysis for acalculous cholecytitis and the continuous monitoring of the present invention continues for other possible etiologies of infection 618.

Referring to FIG. 6B, if the patient has not had a previous cholecystectomy, the DSA accesses the patient datastore and acquires data indicative of whether the patient has any of a set of risk factors 620. In another embodiment of the present invention, the risk factors comprise: 1) Prolonged intensive care unit (ICU) stay (defined as greater than six (6) days); 2) recent surgery within the last two weeks (particularly aortic cross clamp procedures); 3) hypotension (BP less than 90 mmHg); 4) positive end-expiratory pressure (PEEP) greater than ten (10) centimeters (cm); 5) transfusion greater than six (6) units of blood; 6) inability to use the gastrointestinal (GI) tract for nutrition; or 7) immunosuppresssion (AIDS, transplantation, or leukemia).

If the data are sufficient, a determination is made whether the patient has any of the risk factors 626. If the patient does not have any of the risk factors, the diagnostic process is then complete and the continuous monitoring of the present invention continues 628.

If the patient has any of the seven risk factors, the DSA accesses the patient data datastore and acquires data indicative of whether the patient has any of a set of symptoms 630 or abnormal laboratory values. A determination is made whether the data is sufficient to determine whether the patient has any of the symptoms 632 or abnormal laboratory values. If the data necessary to make the decision are not available, the DSA directs the order writing software 415 (see FIG. 4) to order the tests 633. Results are sent to the datastore. Notations of "incomplete data" are kept by the system so that treatment records and need for tests can be audited. This is accomplished by storing an "incomplete data" record 634. Alternatively, an alert may be issued on a monitor at the command center to check for right upper quadrant tenderness although this is not a requirement for further tests to be ordered. In another embodiment of the present invention, the symptoms comprise: right upper quadrant (RUQ) tenderness and the abnormal laboratory results comprising elevated alkaline phosphatase; elevated bilirubin; or elevated liver transaminases.

If the data are sufficient, a determination is made whether the patient has any of the symptoms 636 or abnormal laboratory values. If the patient does not have any of the symptoms or abnormal laboratory values, the DSA concludes that it is very unlikely that the patient has acalculous cholecystitis. The process is then complete and the continuous monitoring of the present invention continues 638.

Figure 6C:
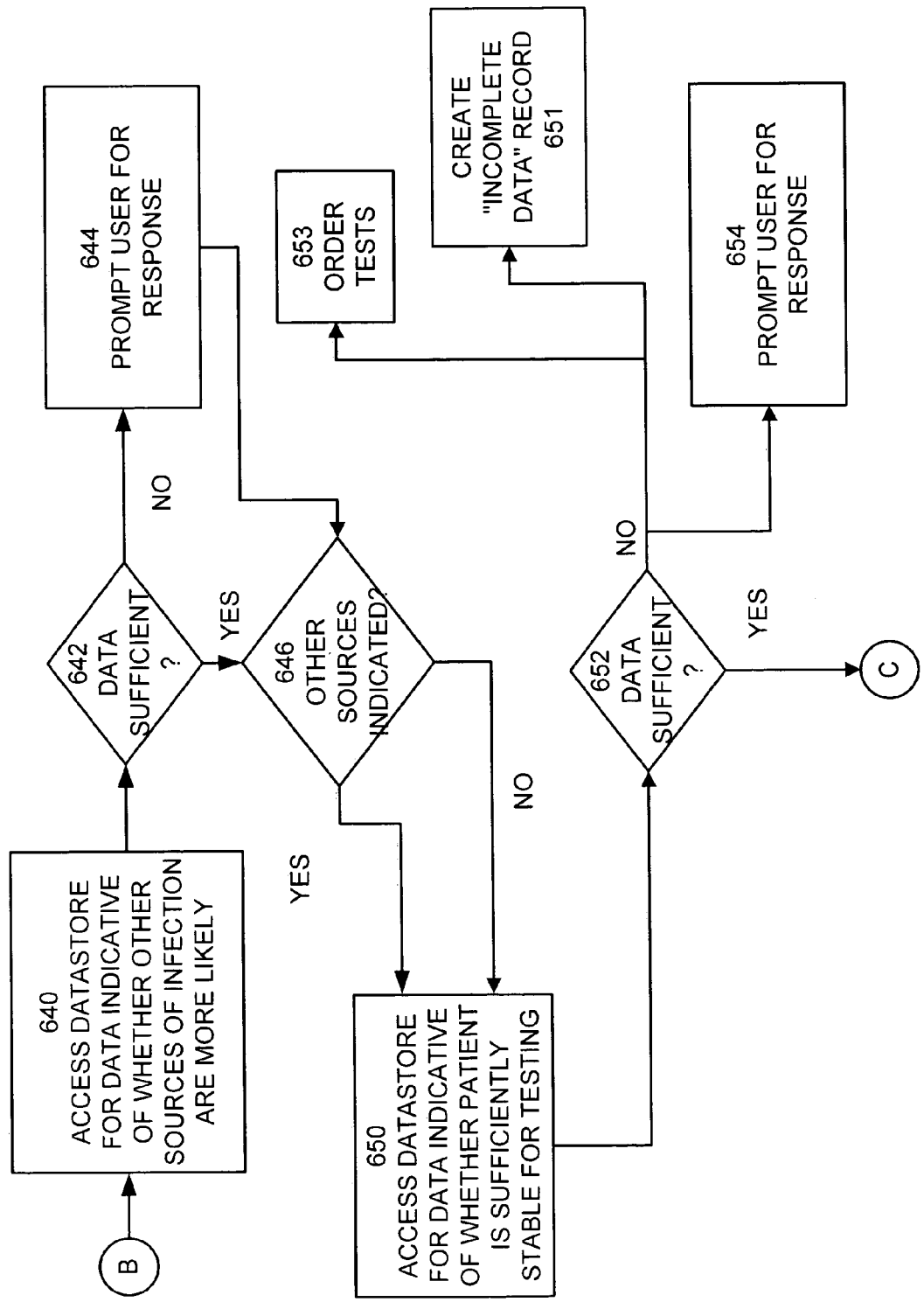

Referring to FIG. 6C, if the patient has any of the symptoms or abnormal laboratory values, the DSA accesses the patient data datastore and acquires data indicative of whether alternative intra-abdominal infectious sources are more likely 640. A determination is made whether the data is sufficient to determine whether the other infectious sources are more likely 642. If the data necessary to make the decision are not available, the DSA prompts the user for a response as to whether other infectious causes are present and considered more likely 644. The user can then provide the requested information that can be considered by the system 646 for further analysis.

If the data are sufficient, a determination is made whether other sources of infection are more likely 646. Regardless of the outcome of this determination, the DSA accesses the patient datastore and acquires data indicative of whether the patient is sufficiently stable to be subjected to testing outside of the critical care environment 650. A determination is made whether the data are sufficient to determine whether the patient is stable to go outside of the critical care environment 652. If the data necessary to make the decision are not available, the DSA prompts the user for a response 654 and may direct the order writing software 415 (see FIG. 4) to order tests or procedures 653 that will assist in such a determination. An "incomplete data" record is also created 651. Test results are sent to the datastore. Notations of "incomplete data" are kept by the system so that treatment records and need for tests can be audited. This is accomplished by storing an "incomplete data" record 654. Alternatively, an alert may be issued on a monitor at the command center although this is not a requirement for further tests to be ordered.

Figure 6D:
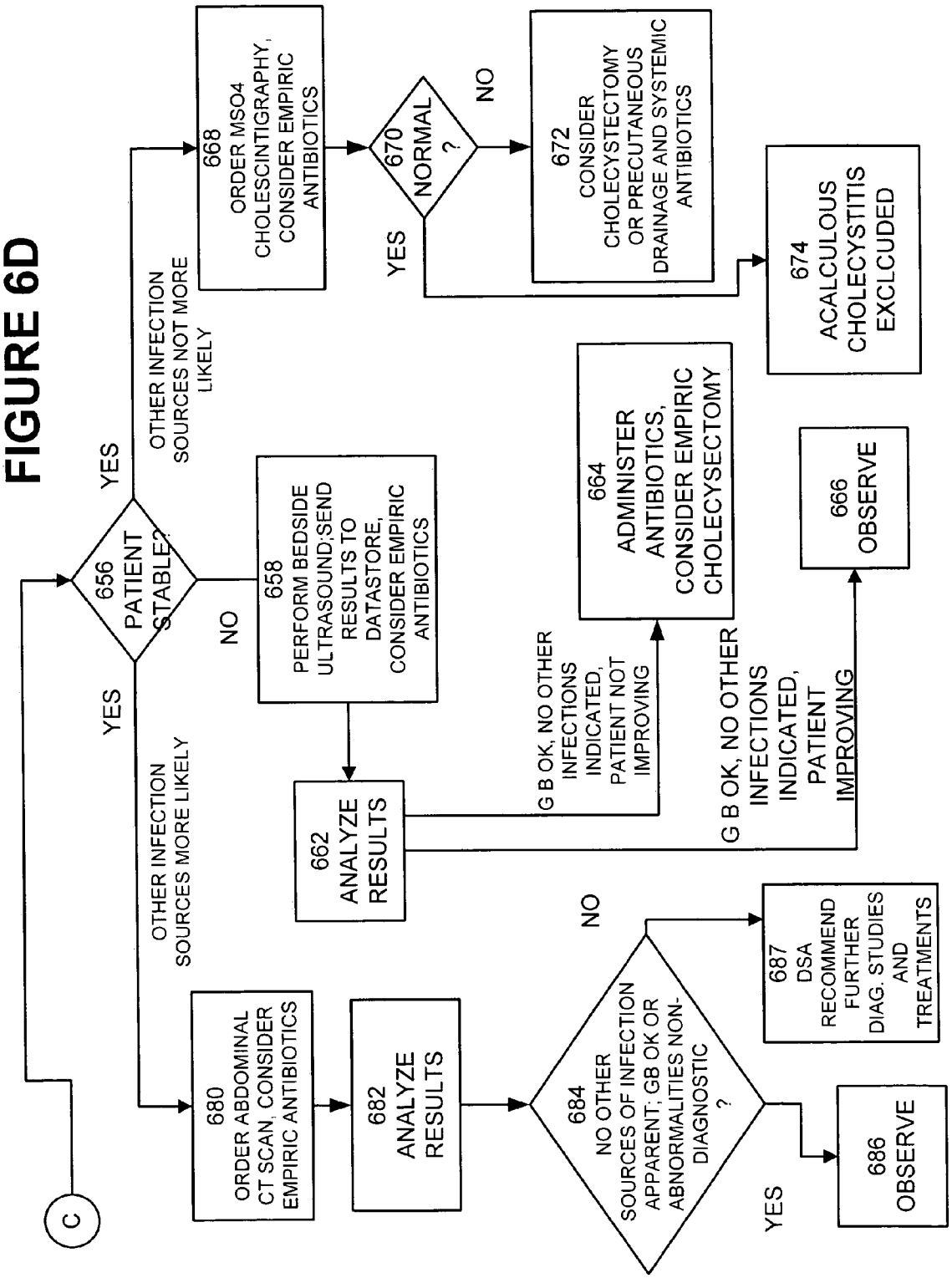

Referring to FIG. 6D, if the data are sufficient, a determination is made whether the patient is sufficiently stable to be subjected to testing outside of the critical care environment 656.

If the patient is not sufficiently stable to be subjected to testing outside of the critical care environment (regardless of whether other sources of infection are indicated), the DSA issues a message comprising a recommendation that empiric antibiotic be considered and a bedside ultrasound be performed and the results communicated to the patient datastore 658. In still another embodiment of the present invention, the DSA directs the order writing software (see FIG. 4) to order the bedside ultrasound. The DSA accesses the test results and other patient data 662. If no other infectious etiologies are identified, no abnormalities of the gall-bladder are noted, and the patient is not improving, the DSA issues a message comprising a "provisional diagnosis of acalculous cholecystitis" and recommends an empiric cholecystectomy and systemic antibiotics 664. If no other infectious etiologies are identified, no abnormalities of the gall bladder are noted, and the patient is improving, the DSA issues a message comprising a recommendation to observe the patient 666.

If the patient is sufficiently stable to go outside of the critical care environment for a test and a determination was made that no other sources of infection were indicated (see FIG. 6C, 646), the DSA issues an order that empiric antibiotics be considered and a morphine sulfate Cholescintigraphy test be performed 668 and the results communicated to the datastore. In still another embodiment of the present invention, the DSA directs the order writing software 415 (see FIG. 4) to order the test.

A determination is made whether the results of the tests are normal 670. If the test indicates an abnormality, the DSA issues a message comprising a recommendation to consider a diagnosis of acalculous cholecystitis, administer systemic antibiotics and perform either a cholecystectomy or a percutaneous drainage 672. If the results are normal, acalculous cholecystitis is excluded 674. The process is then complete and the continuous monitoring of the present invention continues.

If the patient is sufficiently stable to go outside of the critical care environment for a test and a determination was made that other sources of infection were indicated (see FIG. 6C, 646), the DSA issues an order to consider empiric antibiotics and for an abdominal CT scan to be performed 680 and the results communicated to the datastore. In still another embodiment of the present invention, the DSA directs the order writing software 415 (see FIG. 4) to order the test.

The test results and other data are analyzed 682 and a determination is made whether other infection sources are indicated and whether the gall bladder is normal or if abnormalities are present that are not diagnostic 684. If other infectious etiologies are not apparent and the test: a) demonstrates abnormalities of the gall bladder but not diagnostic; or b) no gall-bladder abnormalities are noted, the DSA issues a report comprising a recommendation to maintain continued observation of the patient 686. The process is then complete and the continuous monitoring of the present invention continues. Alternatively, if other infectious etiologies are apparent, the DSA will make recommendations as to further diagnostics and treatments.

While the decision support algorithm described with reference to FIGS. 6A, B, C and 6D refers to a continuous monitoring "mode" of the present invention, this is not meant as a limitation. As previously described, embodiments of the present invention anticipate environments in which data is stored and evaluated on a "delayed" basis. The decision support algorithms described with reference to FIGS. 6A, B, C and 6D may be adapted to operate with delayed data without departing from the scope of the present invention.

Referring again to FIGS. 1 and 2, the remote command center comprises an A/V conferencing server 190. In an embodiment of the present invention, A/V conferencing server 190 acquires audio and video signals from patient monitoring station "A" and provides a terminal (not shown) access to these signals via external network access 195. In yet another embodiment of the present invention addition, a local terminal (not shown) operated by a "local visitation participant" or "LVP" and a remote terminal (not shown) operated by a "remote visitation participant" or "RVP" are bridged by A/V conferencing server 190 to provide audio and video signals from the patient monitoring station, the local terminal and the remote terminal available simultaneously to LVP and RVP. Additionally, a terminal user may control the position of camera 205. By way of illustration and not as a limitation, RVPs may be family members or other concerned parties while LVPs may be patients, nurses, doctors, family members or other concerned parties. This embodiment thus permits family members the capability to "virtually visit" other sick family members when a physical visit to a patient's location is not possible and/or desirable. The "virtual visit" further allows the possibility to see and speak with a care provider regarding a patient's care or related subjects without having to be physically located at the health care provider's location. The present invention also provides a means for the floor staff (i.e. those caregivers in the hospital at or near the patient's bedside) to instantly alert the command center of the conditions of patients who destabilize thereby allowing for more rapid response by those manning the command center.

When each command center person logs onto the system of the present invention, a background service is started. This service subscribes to an emergency alert server that is connected to a video server. As noted earlier, the video server provides video feed from each beside to the command center as needed. Emergency message are passed from the bedside through the video server to the command center. As the emergency alert server receives a message from a video server, it sends a message to all of the subscribed services in the command center. This notification alerts the command center users by means of a "pop-up" alert window at the users' workstation that an emergency condition exists at the bed calling for the alert, and that the floor caregiver has requested immediate backup.

To facilitate the emergency call capability of the present invention, in addition to the various network connections of a more automated type, an emergency "call button" is provided at each critical care location. This could by or near each bed, at a nurse's station, at a mobile care bed or any location where the patient may be located. When pressed, the call button causes a message to be sent to the emergency alert server at the command center that a patient emergency has occurred.

The present invention comprises a video/audio server (Axis 2401) dedicated to each critical care location. A button activation mechanism and associated wiring is provided to allow the call button to be positioned in the room at a location convenient to the caregiver calling for command center backup.

Currently each video server can support up to 16 call buttons by using combinations of the four inputs to signify one alarm in a 4-bit binary pattern although this is not meant as a limitation. A typical installation would use one button or perhaps two (e.g. two beds per room) per video server.

A software interrupt event handler is configured on the video server to respond to activation of the emergency call button.

The emergency alert server comprises a web service called for sending emergency alert signals that is placed in service at system startup. When called, emergency alert web service responds with an acknowledgement message (e.g. "Alert Received"). The emergency alert web service identifies the ward and bed directly from the IP address (unique to each video server) and input number it was passed. It then sends a message to all subscribing clients identifying the emergency condition, the ward, and bed.

When a user logs into a workstation at the command center a user alert service subscribes to the emergency alert server and waits for any emergency message in the background. Upon receiving an emergency message, the service will popup a window with the message on top of the desktop and stay there until the user dismisses or acknowledges the alert. The user alert service the loads video assessment module to allow the command center to view the bed with the emergency.

In another embodiment of the present invention, a critical care hospital bed comprises monitoring instruments linked to a wireless network. This serves the needs of those patients who are transported from one location to another (either internal to a hospital or to other hospitals or diagnostic centers) for testing, procedures or other reasons. In this embodiment, monitoring continues using typical monitoring means that have been described above which include, without limitation, physiological monitoring equipment, video monitoring equipment and an emergency call button, all of which transmit their signals in a wireless fashion so that movement of the patient bed does not interrupt the transmission of information.

A telecommunications network for remote patient monitoring has now been illustrated. It will be apparent to those skilled in the art that other variations of the present invention are possible without departing from the scope of the invention as disclosed. For example, one can envision different ratios of remote command center to patient monitoring stations. Certain types of decision support algorithms would be used by intensivists, other types of remote monitoring of not only patient monitoring stations but other types of hospital functions as well as industrial functions where critical expertise is in limited supply but where that expertise must be applied to ongoing processes. In such cases a system such as that described can be employed to monitor processes and to provide standardized interventions across a number of locations and operations. Further, any reference to claim elements in the singular, for example, using the articles "a," "an," or "the" is not to be construed as limiting the element to the singular.

What is claimed is:

1. A system for determining a treatment plan for a patient comprising:
  a network;
  a datastore accessible to a remote command center via the network, wherein the datastore comprises assessment data elements indicative of medical conditions associated with geographically dispersed patients;
  a decision support system at the remote command center, wherein the decision support system is connected to the network and comprises a software module, wherein the software module comprises instructions for:
    continuously applying a predictive model to a first set of selected assessment data elements to produce current health measures for the patient; and
    utilizing the health measures to produce a treatment plan for the patient, wherein the treatment plan is continuously updated based on the current health measures; and
  a rules generator connected to the network, wherein the rules generator comprises instructions for establishing a patient-specific rule for the patient consistent with the treatment plan for the patient; and
  a rules engine at the remote command center, wherein the rules engine is connected to the network and comprises instructions for:
    applying the patient-specific rule continuously to a second set of selected assessment data elements;
    determining in an automated fashion 24 hours per day 7 days per week whether the patient-specific rule for the patient has been contravened; and
    issuing an alert if the patient-specific rule for the patient has been contravened.

2. The system of claim 1, wherein the predictive model is selected from the group consisting of an APACHE II algorithm; an APACHE III algorithm; a history of present illness (HPI) algorithm; a review of systems (ROS) algorithm; a past, family, and/or social history (PFSH) algorithm; a Sequential Organ Failure Assessment (SOFA) model, and a mortality prediction model (MPM) algorithm.

3. The system of claim 1, wherein the predictive model comprises a guideline selected from the list consisting of: Acalculous Cholecystitis, Acute Pancreatitis Algorithms, Acute Renal Failure-Diagnosis, Acute Renal Failure-Management & Treatment, Adrenal Insufficiency, Agitation and Anxiety, Depression & Withdrawal, Aminoglycoside Dosing and Therapeutic Monitoring, an Amphotericin-B Treatment Guidelines, Analgesia, Antibiotic Classification & Costs, Antibiograms Algorithm, Antibiotic associated Colitis Algorithm, ARDS: Hemodynamic Management, ARDS: Steroid Use, ARDS: Ventilator Strategies, Asthma, Bleeding Patient, Bloodstream Infections, Blunt Cardiac Injury, Bradyarrhythmias, Brain Death, Bronchodilator Use in Ventilator Patients, Bronchoscopy & Thoracentesis Guidelines, Candiduria, Cardiogenic Shock, CardioPulmonary Resuscitation Guideline, Catheter Related Septicemia, a Catheter Replacement Strategies, Cervical Cord Injury, Congestive Heart Failure, COPD Exacerbation & Treatment, CXR (Indications), Dealing with Difficult patients and families, Diabetic Ketoacidosis, Dialysis, Diuretic Use, Drug Changes with Renal Dysfunction, Emergency Cardiac Pacing, Endocarditis Diagnosis and Treatment, Endocarditis Prophylaxis, End of Life Decisions, Endotracheal Tubes & Tracheotomy, Ethical Guidelines, Febrile Neutropenia, FUO, Fluid Resuscitation, Guillain-Barre Syndrome, Heparin, Heparin-Induced Thrombocytopenia, Hepatic Encephalopathy, Hepatic Failure, HIV+Patient Infections, Hypercalcemia Diagnosis and Treatment, Hyperglycemia Insulin Treatment, Hyperkalemia: Etiology & Treatment, Hypernatremia: Etiology & Treatment, Hypertensive Crisis, Hypokalemia: Etiology & Treatment, Hyponatremia: Etiology & Treatment, Hypothermia, Identification of Cervical Cord Injury, Implantable Cardio-defibrillator, Intra-Aortic Balloon Device, Intracerebral Hemorrhage, Latex Allergy, Magnesium Administration, Management of Hypotension, Inotropes, Management of Patients with Ascites, Empiric Meningitis, Meningitis, a Myasthenia Gravis, Myocardial Infarction, Myocardial Infarction with left bundle branch block, Necrotizing Soft Tissue Infections, Neuromuscular Blockers, Neuromuscular Complications of Critical Illness, Non-Infectious Causes of Fever, Non-Traumatic Coma, Noninvasive Modes of Ventilation, Nutritional Management, Obstetrical Complication, Oliguria, Open Fractures, Ophthalmic Infections, Organ Procurement Guidelines, PA Catheter Guideline and Troubleshooting, Pancreatitis, Penetrating Abdominal Injury, Penetrating Chest Injury, Penicillin Allergy, Permanent Pacemaker and Indications, Pneumonia Community Acquired, Pneumonia Hospital Acquired, Post-Op Bleeding, Post-Op Hypertension, Post-Op Management of Abdominal Post-Op Management of Carotid, Post-Op Management of Open Heart, Post-Op Management of Thoracotomy, Post-Op Myocardial Ischemia (Non-Cardiac Arrhythmias after Cardiac Surgery), Post-Op Power Weaning, Pressure Ulcers, Pulmonary Embolism Diagnosis, Pulmonary Embolism Treatment, Respiratory Isolation, Sedation, Seizure, Status Epilepticus, Stroke, Sub-Arachnoid Hemorrhage, Supra-Ventricular Tachyarrhythmia, Supra-Ventricular Tachycardia, Wide Complex QRS Tachycardia, Therapeutic Drug Monitoring, Thrombocytopenia, Thrombolytic Therapy, Transfusion Guidelines, Traumatic Brain Injury, Assessment of Sedation, Sedation, Septic Shock, Bolus Sliding, Scale Midazolam, Short Term Sedation Process, Sinusitis, SIRS, Spinal Cord Injury, Steroid Replacement Strategy, Thyroid Disease, Transplant Infection Prophylaxis, Transplant Related Infections, Treatment of Airway Obstruction, Unknown Poisoning, Unstable Angina, Upper GI Bleeding Stress Prophylaxis, Vancomycin, Upper GI Bleeding Non-Variceal, Upper GI Bleeding Variceal, Use of Hematopoietic Growth Factors, Ventilator Weaning, Ventilator Weaning Protocol, Venous Thrombosis Diagnosis and Treatment, Venous Thromboembolism Prophylaxis, Ventricular Arrhythmia, Warfarin, Warfarin Dosing, and Wound Healing Strategies.

4. The system of claim 1, wherein the patient is located at a health care location that is remote from the command center.

5. The system of claim 1 wherein the rules engine further comprises instructions for:
   making a determination whether the patient requires monitoring by the remote command center; and
   in the event the patient does not require monitoring by the remote command center, issuing a release order.

6. The system of claim 1, wherein the alert comprises an instruction to revise the treatment plan.

7. The system of claim 1, wherein the current health measures are indicative of applying medical treatment resources to the patient and wherein the treatment plan comprises applying medical treatment resources to the patient consistent with the medical condition.

8. The system of claim 1, wherein the current health measures are indicative of denying medical treatment resources to the patient, and wherein the treatment plan comprises treating the patient consistent with standards of medical ethics.

9. The system of claim 1, wherein the current health measures are indicative of denying medical treatment resources to the patient, and wherein the treatment plan is modified to withhold further medical treatment resources from the patient and to treat the patient consistent with standards of medical ethics.

10. The system of claim 1, wherein the patient-specific rule for the patient comprises an algorithm.

11. The system of claim 1, wherein the second set of selected assessment data elements comprises a physiological data element of the patient and a clinical data element of the patient.

12. The system of claim 1, wherein the second set of selected assessment data elements comprises a physiological data element of the patient and a medication data element of the patient.

13. The system of claim 1, wherein the second set of selected assessment data elements comprises a physiological data element of the patient and a laboratory data element of the patient.

14. The system of claim 1, wherein the second set of selected assessment data elements comprises a clinical data element of the patient and a laboratory data element of the patient.

15. The system of claim 1, wherein the second set of selected assessment data elements comprise a physiological data element of the patient and another physiological data element of the patient.

16. The system of claim 1, wherein the second set of selected assessment data elements comprises at least two data elements of the patient selected from the group consisting of a physiological data element, a clinical data element of the patient, a medication data element of the patient, and a laboratory data element of the patient.

17. The system of claim 1, wherein the alert comprises a patient intervention order.

18. The system of claim 1, wherein the rules engine further comprises instructions for:
   determining whether the patient requires monitoring by the remote command center; and
   issuing a stop monitoring order in the event the patient does not require monitoring by the remote command center.

19. The system of claim 1, wherein the network is selected from the group consisting of a wired network, a wireless network, a satellite network, a public switched telephone network, an IP network, a packet switched network, a cell phone network, a cable network, and a coax network, a hybrid fiber coax network.

20. The system of claim 1, wherein the first set of selected assessment data elements comprises a physiological data element of the patient and a clinical data element of the patient.

21. The system of claim 1, wherein the first set of selected assessment data elements comprises a physiological data element of the patient and a medication data element of the patient.

22. The system of claim 1, wherein the first set of selected assessment data elements comprises a physiological data element of the patient and a laboratory data element of the patient.

23. The system of claim 1, wherein the first set of selected assessment data elements comprises a clinical data element of the patient and a laboratory data element of the patient.

24. The system of claim 1, wherein the first set of selected assessment data elements comprise a physiological data element of the patient and another physiological data element of the patient.

25. The system of claim 1, wherein the first set of selected assessment data elements comprises at least two data elements of the patient selected from the group consisting of a physiological data element, a clinical data element of the patient, a medication data element of the patient, and a laboratory data element of the patient.

26. The system of claim 1, wherein the health care location is selected from the group consisting of a remote clinic, a doctor's office, a field hospital, a disaster aid station, and a patient transport vehicle.

27. The method for determining a treatment plan for a patient of claim 21, wherein the health care location is selected from the group consisting of a remote clinic, a doctor's office, a field hospital, a disaster aid station, and a patient transport vehicle.

28. The system of claim 1, wherein the remote command center comprises:
   an external network interface, wherein the external network interface comprises instructions for connecting to an external network; and
   instructions for providing a health care provider access to the remote command center via the external network.

29. The system of claim 28, wherein the external network is selected from the group consisting of a wired network, a wireless network, a cable network, a fiber optic network, and the Internet.

30. The system of claim 28, wherein the health care provider is selected from the group consisting of a physician, a nurse, a clinician, a diagnostician, and a intensivist.

31. The system of claim 28, wherein the remote command center further comprises instructions for sending the health care provider the alert if the patient-specific rule for the hospitalized patient has been contravened.

32. A method for determining a treatment plan for a patient comprising:
   storing assessment data elements indicative of a medical conditions associated with geographically dispersed patients in a datastore, wherein the datastore is accessible to a remote command center via a network;
   accessing a first set of assessment data elements indicative of a medical condition associated with the patient;
   continuously applying a predictive model to the first set of selected assessment data elements to produce current health measures for the patient;
   utilizing the health measures to produce a treatment plan for the patient, wherein the treatment plan is continuously updated based on the current health measures; and
   establishing a patient-specific rule for the patient consistent with the treatment plan for the patient;

applying the patient-specific rule continuously to a second set of selected assessment data elements;

determining in an automated fashion at the remote command center 24 hours per day 7 days per week whether the patient-specific rule for the patient has been contravened; and issuing an alert if the patient-specific rule for the patient has been contravened.

33. The method for determining a treatment plan for a patient of claim 32, wherein the predictive model is selected from the group consisting of an APACHE II algorithm; an APACHE III algorithm; a history of present illness (HPI) algorithm; a review of systems (ROS) algorithm; a past, family, and/or social history (PFSH) algorithm; and a mortality prediction model (MPM) algorithm.

34. The method for determining a treatment plan for a patient of claim 32, wherein the predictive model comprises a guideline selected from the list consisting of:

Acalculous Cholecystitis, Acute Pancreatitis Algorithms, Acute Renal Failure-Diagnosis, Acute Renal Failure-Management & Treatment, Adrenal Insufficiency, Agitation and Anxiety, Depression & Withdrawal, Aminoglycoside Dosing and Therapeutic Monitoring, an Amphotericin-B Treatment Guidelines, Analgesia, Antibiotic Classification & Costs, Antibiograms Algorithm, Antibiotic associated Colitis Algorithm, ARDS: Hemodynamic Management, ARDS: Steroid Use, ARDS: Ventilator Strategies, Asthma, Bleeding Patient, Bloodstream Infections, Blunt Cardiac Injury, Bradyarrhythmias, Brain Death, Bronchodilator Use in Ventilator Patients, Bronchoscopy & Thoracentesis Guidelines, Candiduria, Cardiogenic Shock, CardioPulmonary Resuscitation Guideline, Catheter Related Septicemia, a Catheter Replacement Strategies, Cervical Cord Injury, Congestive Heart Failure, COPD Exacerbation & Treatment, CXR (Indications), Dealing with Difficult patients and families, Diabetic Ketoacidosis, Dialysis, Diuretic Use, Drug Changes with Renal Dysfunction, Emergency Cardiac Pacing, Endocarditis Diagnosis and Treatment, Endocarditis Prophylaxis, End of Life Decisions, Endotracheal Tubes & Tracheotomy, Ethical Guidelines, Febrile Neutropenia, FUO, Fluid Resuscitation, Guillain-Barre Syndrome, Heparin, Heparin-Induced Thrombocytopenia, Hepatic Encephalopathy, Hepatic Failure, HIV+Patient Infections, Hypercalcemia Diagnosis and Treatment, Hyperglycemia Insulin Treatment, Hyperkalemia: Etiology & Treatment, Hypernatremia: Etiology & Treatment, Hypertensive Crisis, Hypokalemia: Etiology & Treatment, Hyponatremia: Etiology & Treatment, Hypothermia, Identification of Cervical Cord Injury, Implantable Cardio-defibrillator, Intra-Aortic Balloon Device, Intracerebral Hemorrhage, Latex Allergy, Magnesium Administration, Management of Hypotension, Inotropes, Management of Patients with Ascites, Empiric Meningitis, Meningitis, a Myasthenia Gravis, Myocardial Infarction, Myocardial Infarction with left bundle branch block, Necrotizing Soft Tissue Infections, Neuromuscular Blockers, Neuromuscular Complications of Critical Illness, Non-Infectious Causes of Fever, Non-Traumatic Coma, Noninvasive Modes of Ventilation, Nutritional Management, Obstetrical Complication, Oliguria, Open Fractures, Ophthalmic Infections, Organ Procurement Guidelines, PA Catheter Guideline and Troubleshooting, Pancreatitis, Penetrating Abdominal Injury, Penetrating Chest Injury, Penicillin Allergy, Permanent Pacemaker and Indications, Pneumonia Community Acquired, Pneumonia Hospital Acquired, Post-Op Bleeding, Post-Op Hypertension, Post-Op Management of Abdominal Post-Op Management of Carotid, Post-Op Management of Open Heart, Post-Op Management of Thoracotomy, Post-Op Myocardial Ischemia (Non-Cardiac Arrhythmias after Cardiac Surgery), Post-Op Power Weaning, Pressure Ulcers, Pulmonary Embolism Diagnosis, Pulmonary Embolism Treatment, Respiratory Isolation, Sedation, Seizure, Status Epilepticus, Stroke, Sub-Arachnoid Hemorrhage, Supra-Ventricular Tachyarrhythmia, Supra-Ventricular Tachycardia, Wide Complex QRS Tachycardia, Therapeutic Drug Monitoring, Thrombocytopenia, Thrombolytic Therapy, Transfusion Guidelines, Traumatic Brain Injury, Assessment of Sedation, Sedation, Septic Shock, Bolus Sliding, Scale Midazolam, Short Term Sedation Process, Sinusitis, SIRS, Spinal Cord Injury, Steroid Replacement Strategy, Thyroid Disease, Transplant Infection Prophylaxis, Transplant Related Infections, Treatment of Airway Obstruction, Unknown Poisoning, Unstable Angina, Upper GI Bleeding Stress Prophylaxis, Vancomycin, Upper GI Bleeding Non-Variceal, Upper GI Bleeding Variceal, Use of Hematopoietic Growth Factors, Ventilator Weaning, Ventilator Weaning Protocol, Venous Thrombosis Diagnosis and Treatment, Venous Thromboembolism Prophylaxis, Ventricular Arrhythmia, Warfarin, Warfarin Dosing, and Wound Healing Strategies.

35. The method for determining a treatment plan for a patient of claim 32, wherein the patient is located at a health care location that is remote from the command center.

36. The method for determining a treatment plan for a patient of claim 32, wherein the alert comprises an instruction to revise the treatment plan.

37. The method for determining a treatment plan for a patient of claim 32, wherein the current health measures are indicative of applying medical treatment resources to the patient and wherein the treatment plan comprises applying medical treatment resources to the patient consistent with the medical condition.

38. The method for determining a treatment plan for a patient of claim 32, wherein the current health measures are indicative of denying medical treatment resources to the patient, and wherein the treatment plan comprises treating the patient consistent with standards of medical ethics.

39. The method for determining a treatment plan for a patient of claim 32, wherein the current health measures are indicative of denying medical treatment resources to the patient, and wherein the treatment plan is modified to withhold further medical treatment resources from the patient and to treat the patient consistent with standards of medical ethics.

40. The method for determining a treatment plan for a patient of claim 32, wherein the patient-specific rule for the patient comprises an algorithm.

41. The method for determining a treatment plan for a patient of claim 32, wherein the second set of selected assessment data elements comprises a physiological data element of the patient and a clinical data element of the patient.

42. The method for determining a treatment plan for a patient of claim 32, wherein the second set of selected assessment data elements comprises a physiological data element of the patient and a medication data element of the patient.

43. The method for determining a treatment plan for a patient of claim 32, wherein the second set of selected assessment data elements comprises a physiological data element of the patient and a laboratory data element of the patient.

44. The method for determining a treatment plan for a patient of claim 32, wherein the second set of selected assessment data elements comprises a clinical data element of the patient and a laboratory data element of the patient.

45. The method for determining a treatment plan for a patient of claim 32, wherein the second set of selected assessment data elements comprises a physiological data element of the patient and another physiological data element of the patient.

46. The method for determining a treatment plan for a patient of claim 32, wherein the second set of selected assessment data elements comprises at least two data elements of the patient selected from the group consisting of a physiological data element, a clinical data element of the patient, a medication data element of the patient, and a laboratory data element of the patient.

47. The method for determining a treatment plan for a patient of claim 32, wherein the alert comprises a patient intervention order.

48. The method for determining a treatment plan for a patient of claim 32, the method further comprising:
    making a determination whether the patient requires monitoring by the remote command center; and
    in the event the patient does not require monitoring by the remote command center, issuing a release order.

49. The method for determining a treatment plan for a patient of claim 32, wherein the first set of selected assessment data elements comprises a physiological data element of the patient and a clinical data element of the patient.

50. The method for determining a treatment plan for a patient of claim 32, wherein the first set of selected assessment data elements comprises a physiological data element of the patient and a medication data element of the patient.

51. The method for determining a treatment plan for a patient of claim 32, wherein the first set of selected assessment data elements comprises a physiological data element of the patient and a laboratory data element of the patient.

52. The method for determining a treatment plan for a patient of claim 32, wherein the first set of selected assessment data elements comprises a clinical data element of the patient and a laboratory data element of the patient.

53. The method for determining a treatment plan for a patient of claim 32, wherein the first set of selected assessment data elements comprises a physiological data element of the patient and another physiological data element of the patient.

54. The method for determining a treatment plan for a patient of claim 32, wherein the first set of selected assessment data elements comprises at least two data elements of the patient selected from the group consisting of a physiological data element, a clinical data element of the patient, a medication data element of the patient, and a laboratory data element of the patient.

55. The method for determining a treatment plan for a patient of claim 32 further comprising:
    interfacing with an external network; and
    providing a health care provider access to the remote command center via the external network.

56. The method for determining a treatment plan for a patient of claim 55, wherein the external network is selected from the group consisting of a wired network, a wireless network, a cable network, a fiber optic network, and the Internet.

57. The method for determining a treatment plan for a patient of claim 55, wherein the health care provider is selected from the group consisting of a physician, a nurse, a clinician, a diagnostician, and a intensivist.

58. The method for determining a treatment plan for a patient of claim 55 further comprising sending the health care provider the alert if the patient-specific rule for the hospitalized patient has been contravened.

* * * * *